(12) United States Patent
Schwartz et al.

(10) Patent No.: US 11,491,034 B2
(45) Date of Patent: Nov. 8, 2022

(54) ABSORBABLE INTRAVASCULAR DEVICES THAT SHORTEN UPON EXPANSION CREATING SPACE FOR VASCULAR MOVEMENT

(71) Applicant: EFEMORAL MEDICAL, INC., Los Altos, CA (US)

(72) Inventors: Lewis B. Schwartz, Lake Forest, IL (US); Ivan Tzvetanov, Mountain View, CA (US); Alex Etrada, Menlo Park, CA (US)

(73) Assignee: EFEMORAL MEDICAL, INC., Los Altos, CA (US)

( * ) Notice: Subject to any disclaimer, the term of this patent is extended or adjusted under 35 U.S.C. 154(b) by 0 days.

(21) Appl. No.: 16/972,976

(22) PCT Filed: Jun. 6, 2019

(86) PCT No.: PCT/US2019/035861
§ 371 (c)(1),
(2) Date: Dec. 7, 2020

(87) PCT Pub. No.: WO2019/236900
PCT Pub. Date: Dec. 12, 2019

(65) Prior Publication Data
US 2021/0322189 A1 Oct. 21, 2021

Related U.S. Application Data

(60) Provisional application No. 62/682,727, filed on Jun. 8, 2018.

(51) Int. Cl.
*A61F 2/82* (2013.01)
*A61F 2/915* (2013.01)
(Continued)

(52) U.S. Cl.
CPC .............. *A61F 2/915* (2013.01); *A61F 2/958* (2013.01); *A61F 2/9524* (2020.05);
(Continued)

(58) Field of Classification Search
CPC .................................................. A61F 2002/826
See application file for complete search history.

(56) References Cited

U.S. PATENT DOCUMENTS

2006/0229700 A1* 10/2006 Acosta ...................... A61F 2/97
623/1.11
2010/0082094 A1* 4/2010 Quadri .................. A61F 2/2409
623/1.26
(Continued)

*Primary Examiner* — Rebecca S Preston
(74) *Attorney, Agent, or Firm* — Convergence Intellectual Property Law P.C.; Jonathan Garfinkel

(57) ABSTRACT

A multi-element, vascular stent may be used to maintain or enhance patency of a blood vessel. The stent may be used in peripheral blood vessels, which may be long and/or tortuous. By using multiple, separate stent elements that are balloon expandable, the multi-element stent may be stronger than a traditional self-expanding stent but may also be more flexible, due to its multiple-element configuration, than a traditional balloon-expandable stent. Individual stent elements shorten upon expansion creating a space between stent elements. The distance between stent elements when deployed may be based on characteristics of the stent and the target vessel location such that the stent elements do not touch one another during skeletal movement. Thus, the multi-element, vascular stent described herein may be particularly advantageous for treating long lesions in tortuous peripheral blood vessels.

15 Claims, 20 Drawing Sheets

(51) Int. Cl.
*A61F 2/958* (2013.01)
*A61F 2/95* (2013.01)

(52) U.S. Cl.
CPC .................. *A61F 2002/826* (2013.01); *A61F 2002/91558* (2013.01); *A61F 2002/91566* (2013.01); *A61F 2210/0004* (2013.01); *A61F 2250/001* (2013.01); *A61F 2250/003* (2013.01); *A61F 2250/0039* (2013.01)

(56) References Cited

U.S. PATENT DOCUMENTS

| | | | | |
|---|---|---|---|---|
| 2013/0268045 A1* | 10/2013 | Papp | ................ | A61F 2/915 623/1.11 |
| 2014/0025157 A1* | 1/2014 | Abunassar | ............ | A61F 2/915 623/1.15 |

* cited by examiner

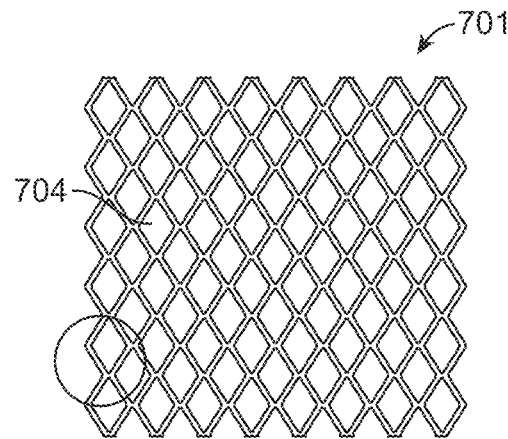
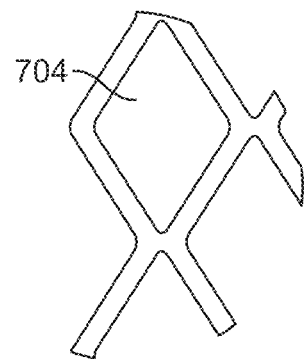
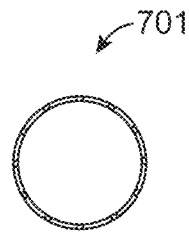
FIG. 7A     FIG. 7B     FIG. 7C
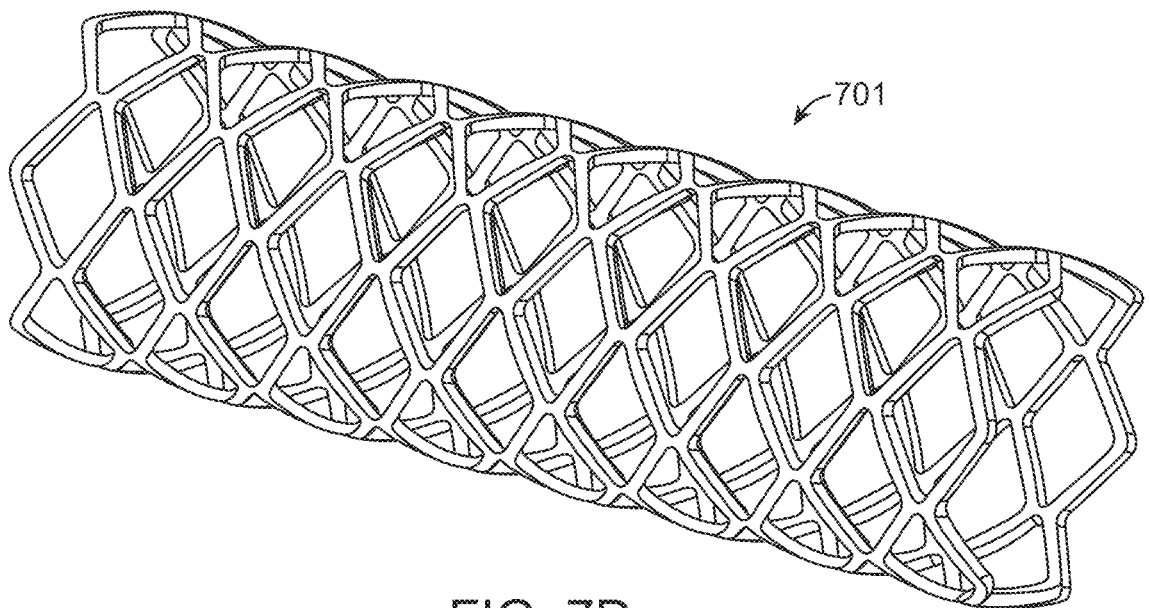
FIG. 7D

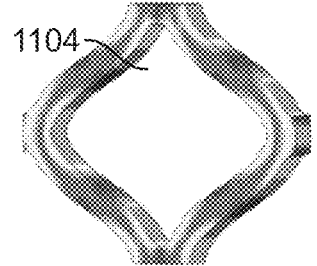
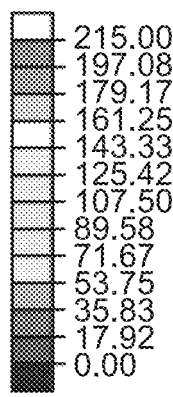
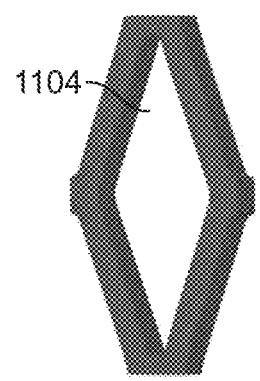
FIG. 11A  FIG. 11B  FIG. 11C
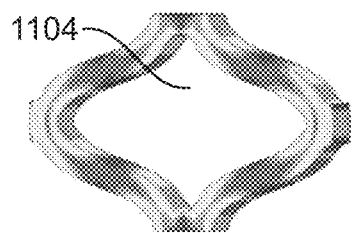
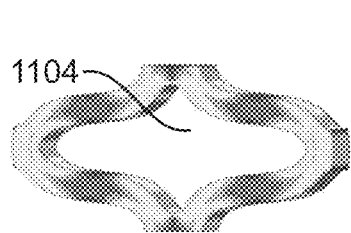
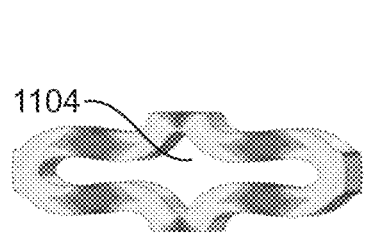
FIG. 11D  FIG. 11E  FIG. 11F

ABSORBABLE INTRAVASCULAR DEVICES THAT SHORTEN UPON EXPANSION CREATING SPACE FOR VASCULAR MOVEMENT

CROSS REFERENCE TO RELATED APPLICATIONS

This application is a 35 U.S.C. § 371 national stage filing of PCT Patent Application Number PCT/US19/35861, filed Jun. 6, 2019, which claims priority to U.S. provisional patent application No. 62/682,727 entitled ABSORBABLE INTRAVASCULAR DEVICES THAT SHORTEN UPON EXPANSION CREATING SPACE FOR VASCULAR MOVEMENT filed on Jun. 8, 2018.

FIELD OF THE INVENTION

The present application pertains generally to the field of medical devices. More specifically, the present application pertains to the design and manufacture of intravascular stents intended to maintain patency (blood flow) of blood vessels (arteries and veins).

BACKGROUND

Atherosclerotic cardiovascular disease or "hardening of the arteries" is the leading cause of death and disability in the world accounting for nearly one-third of all human mortality. Although some developed nations have made significant strides in modifying risk factors and changing lifestyle behaviors, the global prevalence of atherosclerotic disease is still rising with some projections predicting >23 million annual deaths by the year 2030. The economic burden is staggering; in the United States alone, the estimated yearly cost treating atherosclerosis and its sequelae exceeds $200 billion.

Atherosclerosis is a process of pathological arterial aging. In youth, supple elastin fibers within the arterial media provide the structural elasticity and compliance required for arterial pulsation and pulse wave transmission. Over decades, however, the persistent pressure and motion slowly denatures structural matrix proteins causing elastin fatigue and fracture. The result is a slow but inexorable loss of distensibility; the arterial wall chronically stiffens. With the loss of pulsatility and wave reflection, the flow velocity profile becomes blunted; flow reversal is lost and the modulus of antegrade flow is attenuated. This creates long periods of relative stasis in diastole and increasing particle and cellular residence time at the wall. The dysfunctional wall beneath the stagnant boundary layer begins to accumulate circulating atherogenic cholesteryl fatty acyl esters and triglycerides particles, particularly apolipoprotein B-containing lipoproteins. Oxidative modification of the lipoproteins activates the overlying endothelium to secrete chemokines which attract blood-borne monocytes rolling along the endothelium to tether to the vascular surface made sticky by exposure of adhesion molecules and tissue factor. Diapedesis of firmly attached monocytes traps the cells within the thickened subendothelial space. Thus initiated, the ongoing pathological process generates fatty, occlusive lesions via cholesterol-loaded foam cells, continued recruitment and infiltration of inflammatory and hematopoietic cells, and a progressive accumulation of lipid matrix and smooth muscle proliferation that slowly begins to raise the endothelium and encroach upon the arterial lumen. When grown large enough to reduce the flow of blood and oxygen to vital organs, atherosclerotic plaques produce the chronic clinical syndromes of chest pain (angina pectoris), mini-stroke (transient ischemic attack) and poor circulation (claudication). More complex plaques with ossified cores and degenerating fibrous caps can abruptly rupture leading to acute occlusion of the arteries in which they reside. These generate the critical, life-threatening clinical events of heart attack (myocardial infarction), stroke (cerebrovascular accident) and gangrene (critical limb ischemia).

The first stent type to be widely applied to the treatment of atherosclerotic plaques was a balloon-expandable stents (BES) designed as an open mesh tube comprised of stainless steel. When crimped onto an angioplasty balloon it could be advanced through the arterial tree coaxially and deployed directly within the plaque. Stent implantation created a larger and more durable flow channel as compared to balloon angioplasty alone.

In the modern era, balloon-expandable stents are deployed in virtually every case of percutaneous coronary intervention (PCI) and in about half of all peripheral interventional procedures.

In order to prop open large arteries and avoid excessive recoil and deformation, peripheral BES are rigid medical devices. They are typically designed to withstand pressures of $0.5$-$2 \times 10^5$ Pa (375-1500 mmHg, 0.05-0.2 N/mm$^2$), non-physiologic forces that far exceed any intra- or extravascular pressure observed within the human body. In fact, BES are more than ten times rigid than the vessels they occupy. Because they are so rigid, BES can only be implanted in a limited number of anatomic locations, namely those with minimal or highly predictable arterial motion such as the coronary, renal and common iliac arteries. As such, implantation of BES are absolutely contraindicated in a number of important peripheral vascular beds including the carotid, subclavian, external iliac, common femoral, superficial femoral and popliteal arteries.

The rigidity of BES also severely limits their usable length. Implanted stents that are too long will kink or tear arteries in motion leading to restenosis, thrombosis, pseudoaneurysm formation and, in some cases, device fracture and migration. Knowing their dangers, stent manufacturers make their devices available in limited lengths. Although atherosclerotic lesions in peripheral arteries can be several hundred mm long, the longest available BES is only 60 mm. They are clearly inadequate for intervention in the leg where lesions >200 mm are routinely encountered.

As early as 1969, it was theorized that intravascular stents should be flexible rather than rigid. First developed for aerospace applications, an equiatomic alloy made of nickel-titanium called nitinol was thought to exemplify the ideal mechanical properties for the scaffolding of blood vessels. One property was superelasticity, or the ability of a metal to return to its original shape after a substantial deformation. This assured flexibility within arteries in motion within the human body. The other property was shape memory, or the ability of an alloy to be annealed at one temperature, substantially deformed at a lower temperature, then returned to its original shape when heated. This allowed nitinol stents to be compressed into their delivery systems at low temperatures, then released and expanded within the warm mammalian environment at the time of implantation.

The first self-expanding nitinol stent (SES) to be approved for clinical use was a simple, coiled wire made of nitinol. It was introduced into the American market in 1992. Seamless tubes of nitinol became available shortly thereafter, enabling the development of laser-cut, tubular nitinol stents. In the modern era, tubular, nitinol SES are the most common devices deployed in long, flexible blood vessels such as the external iliac and superficial femoral arteries.

Because SES generate much less force than BES, they expand vessels much less completely. In order to get them to expand more fully, SES are routinely post-dilated with high-diameter balloons following their deployment. Even after repeated balloon dilatation, however, the relatively weak SES cannot overcome the inward force of the recoiling artery resulting in an insufficient post-procedure diameter. This is a surprisingly frequent occurrence after SES deployment, especially in peripheral arteries burdened with significant atherosclerosis disease. In one study, underexpansion of the target lesion (≥30% residual stenosis) was observed in 70% of cases after SES implantation into calcific arteries.

The second drawback of the use of nitinol SES is their disquieting tendency toward fracture. Only occasionally observed with BES, SES fracture is alarmingly common, as high as 65% in one clinical report. Although not fully understood, one attractive hypothesis for this phenomenon is that fracture may be a function of the unique biomechanical forces exerted on stents dwelling in the lower extremities. Movement of the legs is a complex motion; loading of the hips and knees during ambulation repeatedly compresses the arteries axially and can even produce multidimensional bends, twists and kinks. The result is single or multiple strut fractures or, in severe cases, complete stent transection. Fracture is more common after implantation of long and/or overlapping stents and, possibly, in more active patients. Fracture of intravascular stents is clearly associated with restenosis, although it remains controversial whether the relationship is associative or causal.

The unique mechanism and design of SES assures that the pattern of chronic forces exerted upon the stented artery are far different than for BES. After deployment of BES, the forces exerted upon the artery are static and temporary. The artery is perturbed by the initial stretch and stent deployment but, once recovered, heals completely and returns to quiescence. Vessels that house a nitinol SES, however, are continually subjected to the chronic outward forces (COF) exerted by the ever-expanding and twisting device. A COF accompanies all SES implantations because, by definition, SES must be "oversized" when implanted. That is to say that the nominal diameter of the stent must, in all cases, exceed the target lesion's reference vessel diameter (RVD) so that the flexible and non-anchored device will remain in place following deployment. Because the final diameter of the device is always less than its nominal "shape memory" diameter when manufactured, it will continue to exert an outward expansive force upon the wall of the vessel until such time that its nominal diameter is reached (if ever). Combined with the motion of the vessels in which SES are typically implanted, this assures a continual and chronic perturbation of the vessel wall for many years following device deployment. The artery responds with chronic inflammation, foreign body reaction, smooth muscle cell proliferation and restenosis. This is particularly troublesome in anatomic areas prone to bending and twisting, such as the common femoral artery. The problem is so prevalent that implantation of nitinol SES at the hip or knee is surgically contraindicated.

Lastly, although nitinol SES are far more flexible than their BES counterparts, continued thickening of arteries treated with SES assures that the stented artery will eventually be rendered more rigid. Even arteries treated with so-called "flexible" stents will generate a significant foreign body response, stiffen, and induce kinking and twisting of the unstented segments. Exaggerated movement of the remaining artery may still allow limited movement and preserve patency, but the resultant aberrant flow patterns and conformations too often lead to thrombosis and failure.

Given the non-physiologic nature of SES in the high-resistance peripheral vasculature, their poor overall effectiveness is not surprising. The one-year primary patency of superficial femoral arteries treated with SES remains a dismal 60% and continues to decline with each successive year.

To address the myriad problems associated with permanent metal implants, stents that slowly dissolve after deployment have long been imagined. So-called "bioresorbable vascular scaffolds" (BVS) potentially offer several key biologic and physiologic advantages including, (1) effective scaffolding without the permanence of a metal implant, (2) attenuation of inflammation and chronic foreign body reaction leading to reduced restenosis and enhanced long-term patency, (3) assistance of adaptive vascular remodeling, (4) restoration of physiologic vasoactive function, and (5) facilitation of imaging and surveillance during follow-up.

The original bioresorbable device was the "catgut" surgical suture, first evident in the historical record some four millennia ago. Catgut sutures are derived from dried sheep, goat or bovine intestine, but have retained the name "catgut" probably because they were also used as strings for musical instruments sometimes referred to as "kits". Catgut sutures are enzymatically degraded and resorbed in vivo so can be classified as bioresorbable. More contemporary bioresorbable surgical sutures are synthetic. Other, more recently developed bioresorbable medical devices includes bioresorbable screws and fracture plates for the treatment of traumatic injuries, indwelling scaffolds that serve as a basis for tissue engineering and regenerative medicine, chemotherapy-loaded polymers for therapeutic oncology, inert synthetic wraps for the prevention of post-operative peritoneal adhesions, bioabsorbable scaffolds for stenting of the upper airways and Eustachian tubes, and bioresorbable intravascular scaffolds (stents). Unfortunately, recent, more longer-term results have raised questions regarding the safety and efficacy of the first-generation absorbable coronary stent.

Therefore, it would be advantageous to have a stent for use in vasculature that is rigid upon implantation so as to maximally dilate and scaffold the artery, but then slowly decreases in rigidity to allow the blood vessel to return to its original, healthy, flexible state. At least some of these objectives will be met by the embodiments described below.

SUMMARY

The embodiments herein describe a device for placement within a blood vessel to maintain or enhance blood flow through the blood vessel. The device may comprise multiple, balloon-expandable, bioresorbable, vascular stent elements configured to be implanted in the blood vessel as a multi-element stent. The stent elements may be positioned serially along a longitudinal length of a balloon with a space between the stent elements in an unexpanded state of 1 mm or less. The stent elements may be configured to shorten upon balloon expansion to an expanded state at a target vessel location to create a space between the stent elements in the expanded state such that the stent elements do not touch one another at the target vessel location during skeletal movement. The stent is configured to be radially rigid and longitudinally flexible after implantation at the target vessel location.

Cell patterns of the stent elements may be configured to shorten the stent elements upon expansion and provide the space between the stent elements in the expanded state. In an embodiment stent elements comprise one or more shortening sections configured to shorten upon expansion to the expanded state and one or more lengthening sections configured to lengthen upon expansion to the expanded state. The shortening section may comprise closed cells. Additionally or alternatively, shortening sections may comprise open cells with one or more struts connecting one or more peaks of a first ring to one or more peaks of a second ring. The lengthening section may comprise open cells with one or more struts connecting one or more valleys of a first ring to one or more valleys of a second ring.

In some embodiments, the stent may be formed from a material comprising poly(L-lactic acid) (PLLA), poly(D-lactic acid) (PDLA), poly(D,L-lactic acid) (PDLLA), semi crystalline polylactide, polyglycolic acid (PGA), poly(lactic-co-glycolic acid) (PLGA), poly(iodinated desamino tyrosyl-tyrosine ethyl ester) carbonate, polycaprolactone (PCL), salicylate based polymer, polydioxanone (PDS), poly(hydroxybutyrate), poly(hydroxybutyrate-co-valerate), poly-orthoester, polyanhydride, poly(glycolic acid-co-trimethylene carbonate), poly(iodinated desaminotyrosyl-tyrosine ethyl ester) carbonate, polyphosphoester, polyphosphoester urethane, poly(amino acids), cyanoacrylates, poly(trimethylene carbonate), poly(iminocarbonate), polyalkylene oxalates, polyphosphazenes, polyiminocarbonates, and aliphatic polycarbonates, fibrin, fibrinogen, cellulose, starch, collagen, polyurethane including polycarbonate urethanes, polyethylene, polyethylene terephthalate, ethylene vinyl acetate, ethylene vinyl alcohol, silicone including polysiloxanes and substituted polysiloxanes, polyethylene oxide, polybutylene terephthalate-co-PEG, PCL-co-PEG, PLA-co-PEG, PLLA-co-PCL, polyacrylates, polyvinyl pyrrolidone, polyacrylamide, or combinations thereof.

In an embodiment, the stent comprises a therapeutic drug. The therapeutic drug may prevent or attenuate inflammation, cell dysfunction, cell activation, cell proliferation, neointimal formation, thickening, late atherosclerotic change or thrombosis.

In an embodiment, the radial rigidity of the stent is slowly attenuated as its structural polymer is unlinked and metabolized such that the stent slowly becomes more flexible causing adaptation and remodeling of the vessel and restoration of the vessel's elasticity.

A method for manufacturing an intravascular stent may comprise loading a multi-element stent comprising multiple individual stent elements onto an inflatable balloon in an expanded state such that the stent elements are positioned serially along a longitudinal length of the balloon and the stent elements do not touch one another. The stent elements may be spaced such that the stent elements do not touch one another at a target vessel location during skeletal movement. The balloon may be deflated and the multi-element crimped to an unexpanded state such that each stent element lengthens and the space between the stent elements is reduced to 1 mm or less.

This and other aspects of the present disclosure are described herein.

BRIEF DESCRIPTION OF THE DRAWINGS

Present embodiments have other advantages and features which will be more readily apparent from the following detailed description and the appended claims, when taken in conjunction with the accompanying drawings, in which:

FIGS. 7A-7D show an embodiment of a stent pattern. FIG. 7A is a two-dimensional depiction of an element. FIG. 7B shows a magnified view of the cells in FIG. 7A. FIGS. 7C and 7D show the stent element of FIG. 7A in cylindrical form.

FIGS. 11A-11F show finite element analysis (FEA) of a bioresorbable polymer stent cell that lengthens upon crimping and shortens upon expansion.

DETAILED DESCRIPTION

Figure 1:
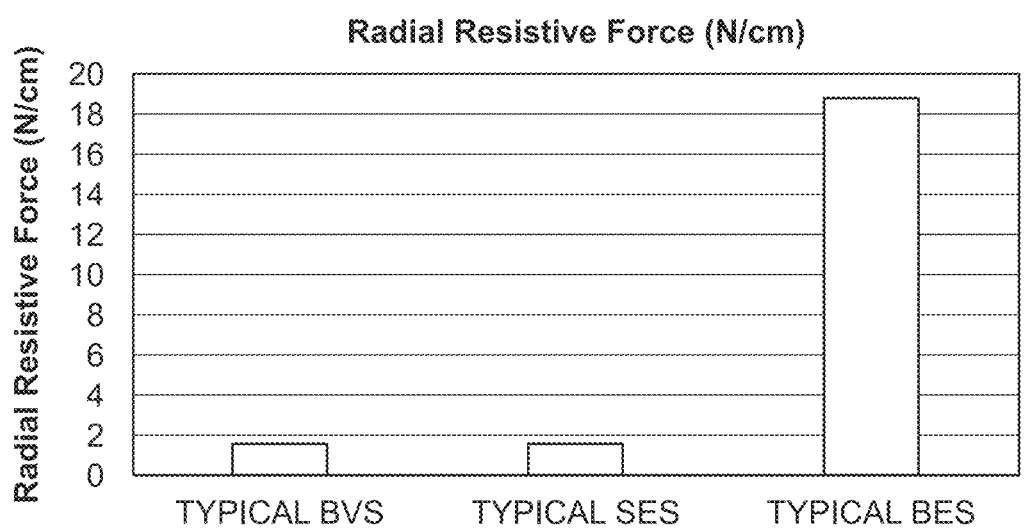
FIG. 1 shows the typical radial resistive forces of intravascular stents.

While the invention has been disclosed with reference to certain embodiments, it will be understood by those skilled in the art that various changes may be made and equivalents may be substituted without departing from the scope of the invention. In addition, many modifications may be made to adapt to a particular situation or material to the teachings of the invention without departing from its scope.

Throughout the specification and claims, the following terms take the meanings explicitly associated herein unless the context clearly dictates otherwise. The meaning of "a", "an", and "the" include plural references. The meaning of "in" includes "in" and "on." Referring to the drawings, like numbers indicate like parts throughout the views. Additionally, a reference to the singular includes a reference to the plural unless otherwise stated or inconsistent with the disclosure herein.

The word "exemplary" is used herein to mean "serving as an example, instance, or illustration." Any implementation described herein as "exemplary" is not necessarily to be construed as advantageous over other implementations.

Various embodiments are described herein with reference to the figures. The figures are not drawn to scale and are only intended to facilitate the description of the embodiments. They are not intended as an exhaustive description of the invention or as a limitation on the scope of the invention. In addition, an illustrated embodiment needs not have all the aspects or advantages shown. An aspect or an advantage described in conjunction with a particular embodiment is not necessarily limited to that embodiment and can be practiced in any other embodiments even if not so illustrated.

FIG. 1 shows the typical radial resistive forces of intravascular stents. A typical "bioresorbable vascular scaffold" (BVS) or absorbable stent has a radial resistive force of under 2 N/cm. Similarly, a typical self-expanding metal stent (SES) has a radial resistive force of under 2 N/cm. Typical balloon-expandable metal stents (BES) have a much higher radial resistive force, sometimes above 18 N/cm.

The embodiments herein describe the design of a new, intravascular absorbable device that maintains the flow channel (patency) of long blood vessels by providing temporary, rigid, radial support that is far greater than that provided by a typical absorbable or metal self-expanding stent (SES) and commensurate with that provided by a metal balloon-expandable stent (BES). Once implanted, the absorbable device imparts a high degree of radial force to prop open the diseased artery; the force is roughly equivalent to a large diameter, peripheral, balloon-expandable metal stent.

In contrast to most stent patterns which are designed to marry both radial force and longitudinal flexibility, the patterns described herein are specifically tailored to maximize radial force and rigidity and forego longitudinal and axial flexibility.

The devices described herein are multi-element, vascular stents (or "vascular scaffolds"). These stents are comprised of multiple, short, rigid, cylindrical stent segments, or elements, which are separate from one another but may be referred to together as a multi-element stent.

Generally, at least two of the elements of the multi-element stent described herein will be sufficiently rigid to provide a desired level of strength to withstand the stresses of the vessel in which they are placed, such as a tortuous peripheral vessel. At the same time, a multi element stent will also be flexible, due to the fact that it is made up of multiple separate elements, thus allowing for placement within a curved, torturous blood vessel. In some embodiments, at least two of the elements vary in rigidity or radial strength in a multi-element stent. In one embodiment, the outer elements may have a lesser radial strength than the inner elements in a multi-element stent. In another embodiment, a multi-element stent comprises elements having an increasing radial strength serially along the length of the multi-element stent, such as in an AV fistula. Thus, the radial strength of elements may vary and be tailored by known characteristics of a target artery.

Additionally, the multi element stents described herein will usually be balloon-expandable rather than self-expanding, since balloon-expandable stents are typically stronger than self-expanding stents. Each balloon expandable element of the stent may have relatively high radial force (rigidity) due to the described structures and materials. A stent element is defined as being radially rigid if it has a radial strength significantly higher than self-expanding stents that is similar or greater in magnitude to that of traditional, metal balloon-expandable stents, such as those made of steel or cobalt-chromium.

When mounted serially on an inflatable balloon, they can be simultaneously implanted side-by-side in long blood vessels. During motion of the organism, the elements can move independently, maintaining their individual shape and strength while the intervening, non-stented elements of the vessel can twist, bend and rotate unencumbered. The result is a treated vessel with a rigidly maintained flow channel that still enjoys unrestricted flexibility during organismal movement.

The described embodiments exploit the principles that, (1) a rigid device that is deployed via balloon-expansion represents the optimal design of an intravascular stent given its transient effect on the arterial wall and relative ease of precise implantation, (2) a long, rigid device cannot be safely implanted in an artery that bends and twists with skeletal motion, (3) long arteries that bend and twist could be effectively treated with multiple, short BES that allow the intervening, non-stented arterial elements to move unencumbered, (4) the length, number and spacing of the stent elements could be determined by the known and predictable bending characteristics of the target arteries, and (5) arteries need only be scaffolded transiently; late dissolution of the stent will have little effect on the long-term effectiveness of treatment.

Figure 2A:
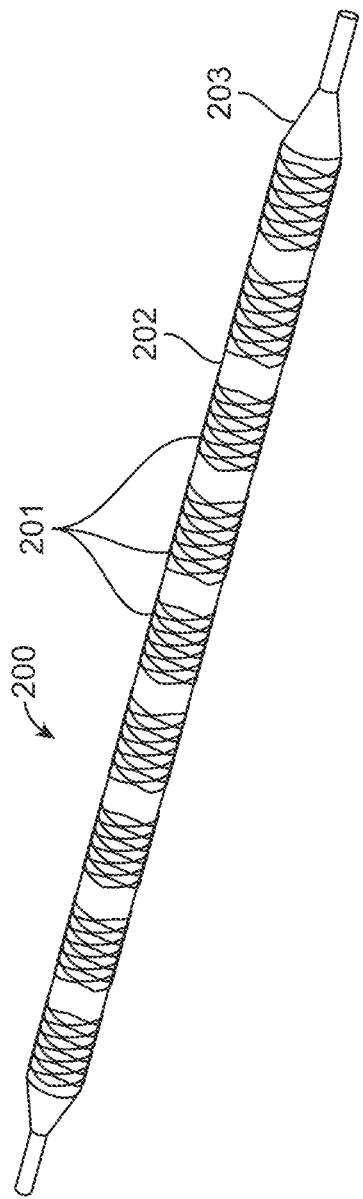
FIG. 2A illustrates one embodiment of a multi-element stent.
Figure 2B:
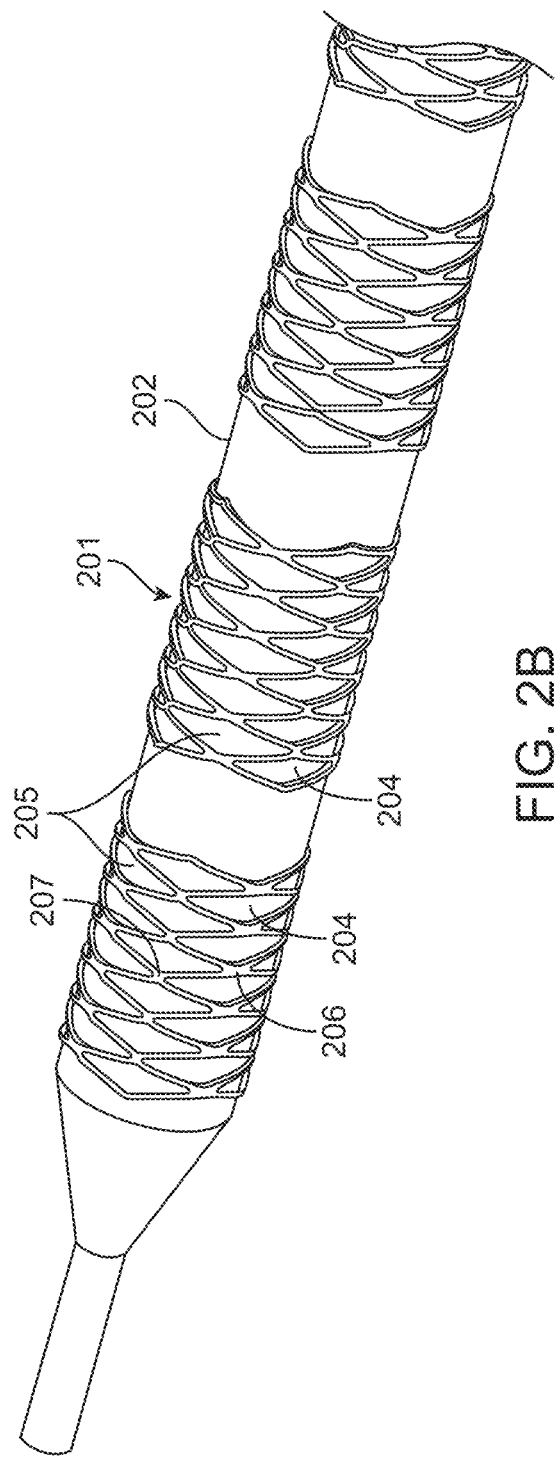
FIG. 2B is a magnified view of the stent elements in FIG. 2A.

One embodiment of the fully assembled device in shown in FIG. 2A. A single balloon inflation and device deployment can treat a long segment of diseased artery while still preserving the critical ability of the artery to bend with skeletal motion such as sitting or walking. Multi-element stent 200 comprises multiple stent elements 201. Individual balloon-expandable stent elements 201 are crimped onto an inflatable balloon 203 to facilitate delivery. FIG. 2B is a magnified view of the stent elements 201 in FIG. 2A. Individual elements 201 are positioned serially along a longitudinal length of the balloon 203 and spaced such that the stent elements 201 do not touch one another. Further, the spacing is such that after deployment, the stent elements 201 do not touch or overlap during skeletal movement. The number of elements 201, length of elements, and gap 202 between elements 201 may vary depending on the target vessel location. In an embodiment, each element 201 in the multi-element stent 200 has the same length. In multi-element stents having three or more elements 201, and thus two or more gaps 202, the gaps may be of the same length.

Figure 3A:
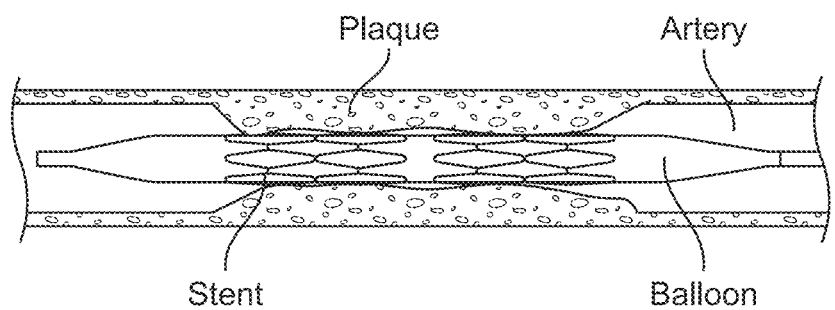
FIGS. 3A-3C depict deployment of a balloon-expandable multi-element stent.
Figure 3B:
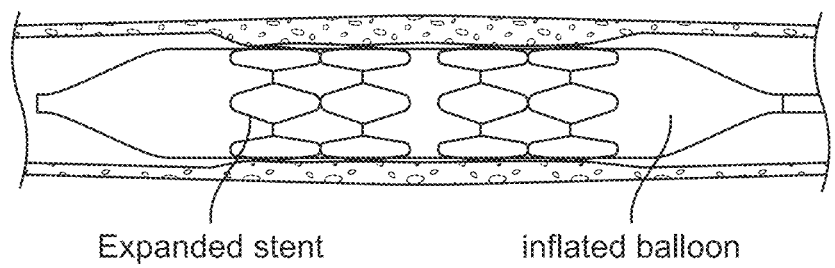
Figure 3C:
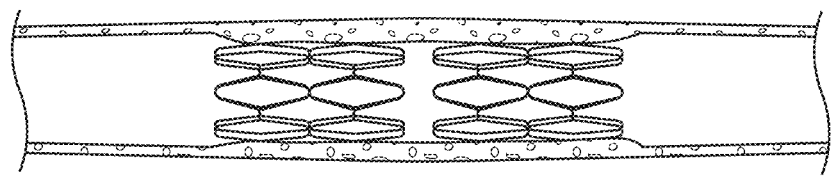

FIGS. 3A-3C depict deployment of a balloon-expandable multi-element stent. In FIG. 3A a multi-element stent mounted on a balloon is advanced to the lesion. In FIG. 3B the balloon and stent are expanded. In FIG. 3C the balloon is withdrawn leaving the multi-element stent still within the artery.

Figure 4A:
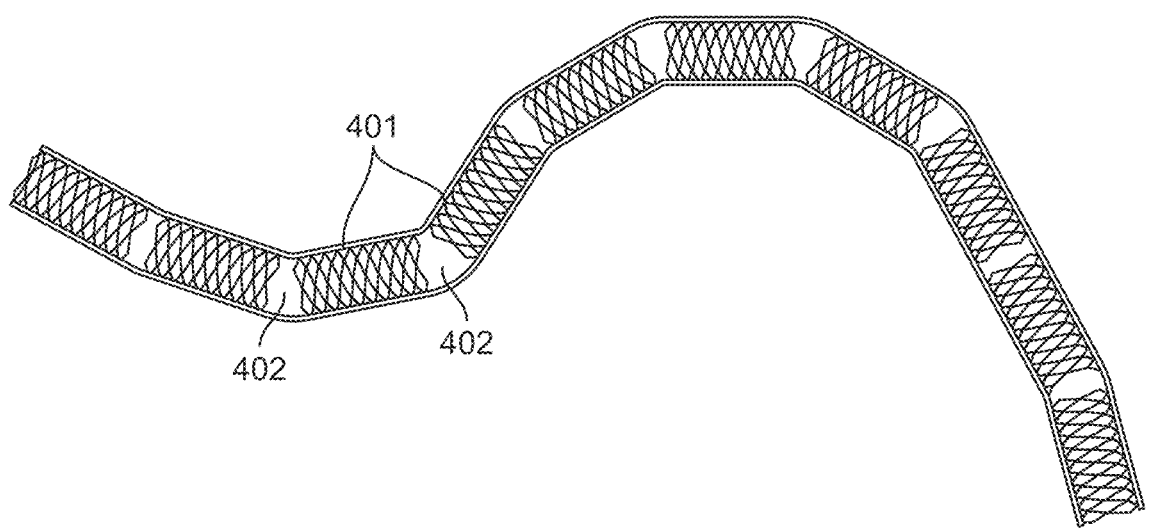
FIG. 4A shows an implanted multi-element stent in a popliteal artery during full flexion of the hip and knee.
Figure 4B:
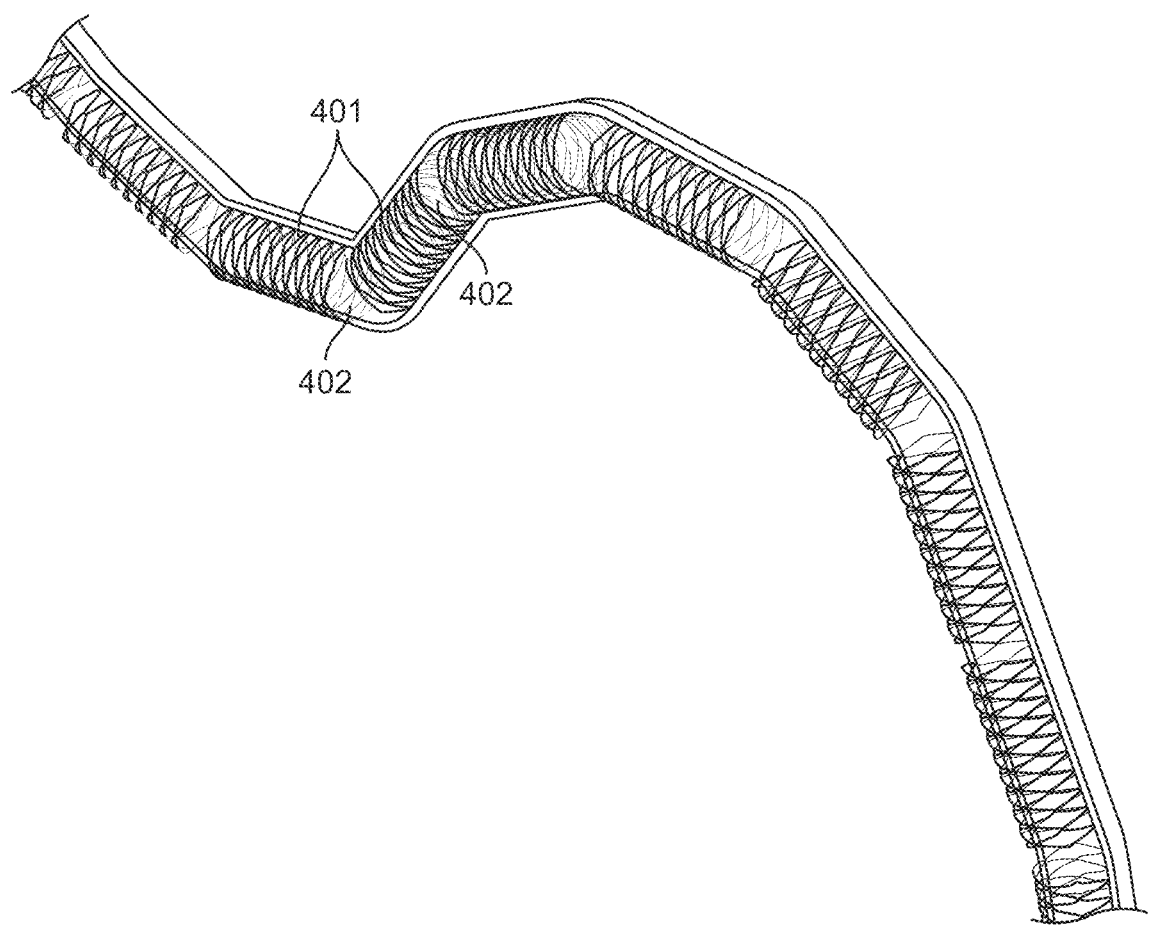
FIG. 4B depicts the implanted device of FIG. 4A shown in three dimensions.

FIG. 4A shows an implanted multi-element stent in a popliteal artery during full flexion of the hip and knee. FIG. 4B depicts the implanted device of FIG. 4A shown in three dimensions. The individual stent elements 401 are spaced such that they do not overlap even when the artery is highly bent. Unencumbered arterial movement is afforded through flexion or extension of the unstented gaps 402.

Proper stent element length and the spacing between stent elements is important given the length and persistent motion of the extremity arteries. If stent elements are too long, the stent will lack sufficient longitudinal flexibility. If the elements are placed too close together, they may overlap during movement leading to a similar lack of sufficient longitudinal flexibility. This may lead to fracture of the stent elements. Fracture of intravascular stents is clearly associated with restenosis. Likewise, if elements are too short or spaced too far apart, the lesion may not be sufficiently contact the target lesion. Proper length and spacing of the elements may be determined by the known characteristics of the target artery.

Figure 5A:
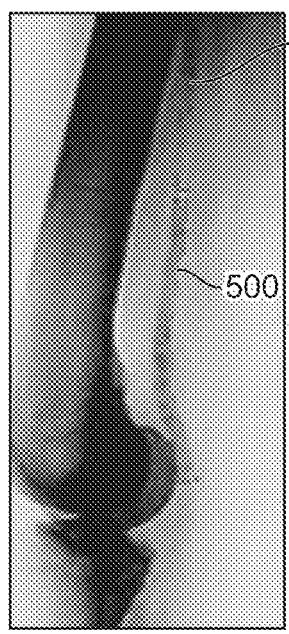
FIGS. 5A-5C are side views of a self-expanding Nitinol stent placed in a distal SFA and popliteal artery, illustrated during different amounts of leg flexion.
Figure 5B:
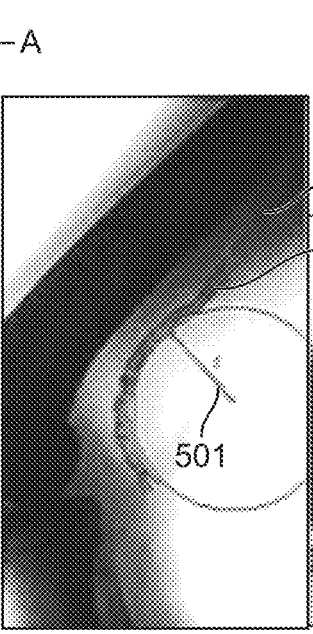
Figure 5C:
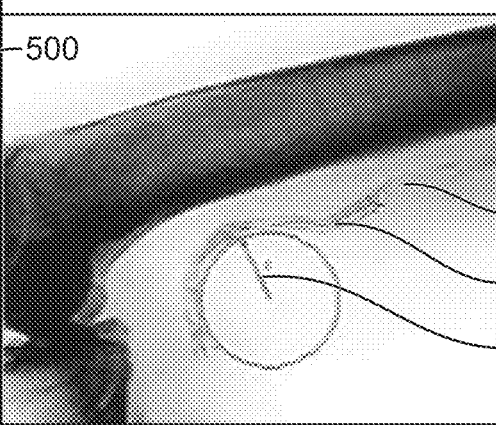

FIGS. 5A-5C are side views of a self-expanding, Nitinol stent 500 placed in a distal SFA and popliteal artery, illustrated during different amounts of leg flexion. FIG. 5A illustrates stent 500 with the leg in the neutral position, minimal flexion/mostly extended. FIG. 5B illustrates stent 500 during partial flexion (70°/20° knee/hip flexion), with a circle and bend radius 502 illustrating the angle of flexion and the curved deformation of stent 600. FIG. 5C illustrates stent 500 during greater flexion (90°/90° knee/hip flexion). As FIGS. 5A-5C illustrate, stent 500 is markedly deformed by movement of the leg. The drawn circle illustrates the use of bend radius 502 to describe the degree of deformation. Stents that bend around a small circle (with a small radius 502) are more deformed, e.g., the more deformed stent in the FIG. 5C has a smaller bend radius 502 than the less deformed stent 500 in FIG. 5B. The nearly straight stent in 5A has a very large bend radius that is too large to be accurately estimated.

Stent deformation after implantation in the femoropopliteal arteries is shown in Table 1. Perfect straightness is assigned a value of 180°. Deflection (°) is calculated as the difference between bend angles during various degrees of extremity flexion. Note the significant bending of popliteal stents as compared to SFA stents.

elements in the device intended for the popliteal artery must be more widely spaced so they won't overlap during skeletal movement.

Figure 6:
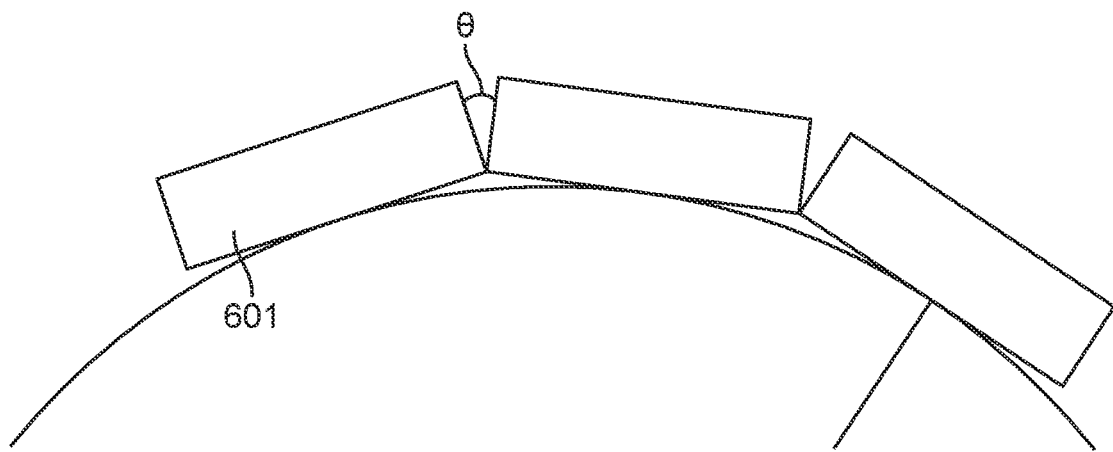
FIG. 6 depicts an angle created between stent elements during maximal flexion of the target vessel location during skeletal movement.
Figure 8A:
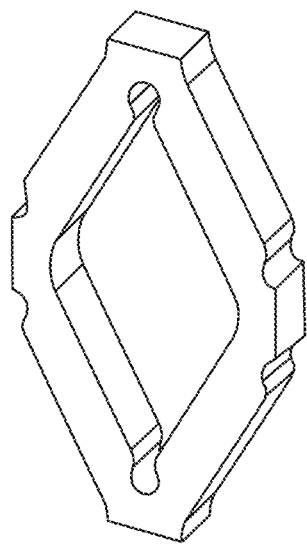
FIGS. 8A-8D show cell views of patterns of stent elements that shorten upon expansion.
Figure 8B:
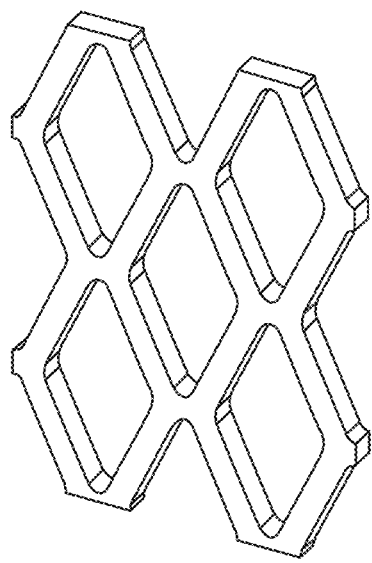
Figure 8C:
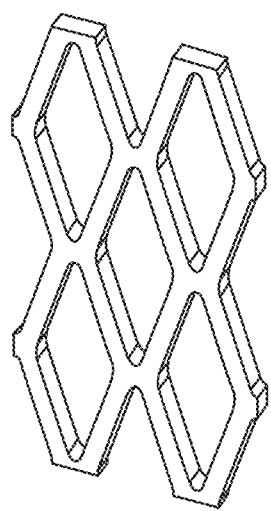
Figure 8D:
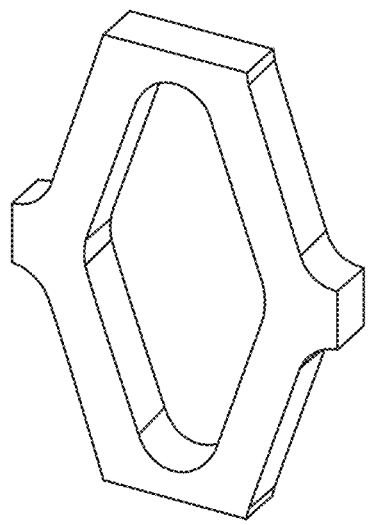

FIG. 6 depicts an angle θ (25.609° as an example in an embodiment shown in FIG. 6) created between stent elements 601 during maximal flexion of the target vessel location during skeletal movement. Angle θ is a calculated angle governed by the maximum bend radius and the maximum individual stent element 601 length for each anatomical location. For the SFA, angle θ is calculated to be 8.473°. For the popliteal, angle θ is calculated to be 25.609°.

In an embodiment, the minimum necessary gap between elements can be calculated using the planned stent diameter (D) in the expanded state at the target vessel location and the angle created between stent elements during maximal flexion of the vessel (θ) at the target vessel location. The gap (G) may be calculated using the formula:

TABLE 1

Stent deformation after implantation in the femoropopliteal arteries.

|  | SFA | SFA/prox pop | popliteal | SFA | SFA/prox pop | popliteal |
| --- | --- | --- | --- | --- | --- | --- |
| N | 11 | 2 | 6 | 11 | 2 | 6 |
|  | Measured bend angle (°) | | | Deflection (°) | | |
| neutral position | 169 ± 6 | 155 ± 11 | 167 ± 7 | | | |
| 70°/20° knee/hip flexion | 168 ± 3 | 146 ± 3 | 137 ± 18 | 4 ± 3 | 9 ± 8 | 29 ± 12* |
| 90°/90° knee/hip flexion | 165 ± 5 | 148 ± 8 | 103 ± 21 | 5 ± 2 | 8 ± 4 | 64 ± 16* |
|  | Measured bend radius (mm) | | | | | |
| 70°/20° knee/hip flexion | NA | NA | 93 ± 52 | | | |
| 90°/90° knee/hip flexion | 135 ± 54** | NA | 22 ± 2 | | | |

Sample sizes refer to the number of treated lesions. Data are presented as mean ± SD. NA—not applicable (stent bending deformations are minimal and bending radii are too large to be accurately measured).
*p < 0.05 as compared to SFA or SFA/prox pop.
**Stent bending radii measurable in 7 cases The length and spacing of the individual elements is partially determined by the planned anatomic location of the device. For instance, available anatomic and physiologic data suggest that the superficial femoral artery (SFA) is only minimally bent and compressed during flexion of the thigh and knee (bending~7° and compression~5%) so individual stent elements in the device intended for the SFA can therefore be fairly closely spaced; they won't overlap even when the leg is bent. In contrast, the popliteal artery more severely deforms when the hip and knee are flexed (bending~60° and compression~8%). Therefore, individual stent $$G = \sqrt{\frac{D^2}{2}(1 - \cos\theta)}$$

As can be seen from the given formula, if all other factors remain the same, the distance between each stent element increases with an increased diameter of the stent element. Similarly, if all other factors remain the same, the distance between each stent element will be larger in the popliteal than the SFA. Table 2 shows calculated gaps using this formula.

TABLE 2

Calculated element spacing taking into account planned stent diameter and the angle created between stent elements during maximal flexion of the vessel

| Intended Anatomic Location | Maximal Deflection (°) | Maximal Bend Radius (mm) | Length (cm) | Diameter (mm) | Element Length (mm) | Number of Elements | Element Spacing (mm) |
| --- | --- | --- | --- | --- | --- | --- | --- |
| SFA | 8 | 135 | 30 | 5.0 | 15 | 2 | 0.37 |
| SFA | 8 | 135 | 30 | 6.0 | 15 | 2 | 0.44 |
| SFA | 8 | 135 | 40 | 5.0 | 20 | 2 | 0.37 |
| SFA | 8 | 135 | 40 | 6.0 | 20 | 2 | 0.44 |
| SFA | 8 | 135 | 60 | 5.0 | 20 | 3 | 0.37 |
| SFA | 8 | 135 | 60 | 6.0 | 20 | 3 | 0.44 |
| SFA | 8 | 135 | 80 | 5.0 | 20 | 4 | 0.37 |

TABLE 2-continued

Calculated element spacing taking into account planned stent diameter and the angle created between stent elements during maximal flexion of the vessel

| Intended Anatomic Location | Maximal Deflection (°) | Maximal Bend Radius (mm) | Length (cm) | Diameter (mm) | Element Length (mm) | Number of Elements | Element Spacing (mm) |
|---|---|---|---|---|---|---|---|
| SFA | 8 | 135 | 80 | 6.0 | 20 | 4 | 0.44 |
| SFA | 8 | 135 | 80 | 8.0 | 20 | 4 | 0.59 |
| SFA | 8 | 135 | 100 | 3.0 | 20 | 5 | 0.22 |
| SFA | 8 | 135 | 100 | 4.0 | 20 | 5 | 0.30 |
| SFA | 8 | 135 | 100 | 5.0 | 20 | 5 | 0.37 |
| SFA | 8 | 135 | 100 | 6.0 | 20 | 5 | 0.44 |
| SFA | 8 | 135 | 100 | 8.0 | 20 | 5 | 0.59 |
| Popliteal | 64 | 22 | 20 | 4.0 | 10 | 2 | 0.89 |
| Popliteal | 64 | 22 | 20 | 5.0 | 10 | 2 | 1.11 |
| Popliteal | 64 | 22 | 30 | 4.0 | 10 | 3 | 0.89 |
| Popliteal | 64 | 22 | 30 | 5.0 | 10 | 3 | 1.11 |
| Popliteal | 64 | 22 | 40 | 4.0 | 10 | 4 | 0.89 |
| Popliteal | 64 | 22 | 40 | 5.0 | 10 | 4 | 1.11 |
| Popliteal | 64 | 22 | 60 | 4.0 | 10 | 6 | 0.89 |
| Popliteal | 64 | 22 | 60 | 5.0 | 10 | 6 | 1.11 |
| Popliteal | 64 | 22 | 80 | 4.0 | 10 | 8 | 0.89 |
| Popliteal | 64 | 22 | 80 | 5.0 | 10 | 8 | 1.11 |
| Popliteal | 64 | 22 | 100 | 3.0 | 10 | 10 | 0.66 |
| Popliteal | 64 | 22 | 100 | 4.0 | 10 | 10 | 0.89 |
| Popliteal | 64 | 22 | 100 | 5.0 | 10 | 10 | 1.11 |
| Popliteal | 64 | 22 | 100 | 6.0 | 10 | 10 | 1.33 |
| Popliteal | 64 | 22 | 100 | 8.0 | 10 | 10 | 1.77 |

Ideal gap length between stent elements may also be influenced by axial stent compression or shortening during extremity flexion. Table 3 shows axial stent compression after implantation in the femoropopliteal arteries. The amount of axial compression is calculated as the difference between measured stent lengths during various degrees of extremity flexion.

Ideal gap length taking into account axial compression may be calculated using the formula:

$$Gap = ((LEC + GEC - GC)/(e-1)) + G$$

L is the stent element length. E is the number of stent elements. G is the gap length calculated using the previous formula. C is the maximum percent axial compression for

TABLE 3

Axial stent compression after implantation in the femoropopliteal arteries

| | Measured stent length (mm) | | | Axial compression (%) | | |
|---|---|---|---|---|---|---|
| | SFA | SFA/prox pop | popliteal | SFA | SFA/prox pop | popliteal |
| Single 80 mm stents | | | | | | |
| N | 6 | 1 | 1 | 6 | 1 | 1 |
| neutral position | 80 ± 2 | 73 | 79 | | | |
| 70°/20° knee/hip flexion | 78 ± 2 | 72 | 76 | 2.0 ± 1.8 | 2.7 | 3.1 |
| 90°/90° knee/hip flexion | 77 ± 2 | 70 | 71 | 3.5 ± 2.1 | 5.0 | 9.3 |
| Single 100 mm stents | | | | | | |
| N | 4 | 1 | 3 | 4 | 1 | 3 |
| neutral position | 101 ± 2 | 94 | 100 ± 3 | | | |
| 70°/20° knee/hip flexion | 99 ± 3 | 92 | 98 ± 1 | 1.4 ± 1.9 | 2.1 | 2.0 ± 1.7 |
| 90°/90° knee/hip flexion | 98 ± 1 | 88 | 92 ± 6 | 2.9 ± 1.4 | 5.7 | 8.4 ± 5.0 |
| Overlapped stents | | | | | | |
| N | 1 | | 2 | 1 | | 2 |
| neutral position | 96.6 | | 118 ± 75 | | | |
| 70°/20° knee/hip flexion | 96.5 | | 112 ± 74 | 0.1 | | 6.1 ± 3.0 |
| 90°/90° knee/hip flexion | 89.8 | | 108 ± 70 | 7.0 | | 8.4 ± 1.6 |
| All stents (including overlapped) | | | | | | |
| N | 11 | 2 | 6 | 11 | 2 | 6 |
| neutral position | 91 ± 14 | 84 ± 14 | 102 ± 36 | | | |
| 70°/20° knee/hip flexion | 90 ± 15 | 82 ± 14 | 99 ± 35 | 1.7 ± 1.7 | 2.4 ± 0.4 | 3.5 ± 2.7 |
| 90°/90° knee/hip flexion | 88 ± 15 | 79 ± 13 | 94 ± 35 | 3.1 ± 1.8 | 5.3 ± 0.5 | 8.5 ± 3.2* |

Sample sizes refer to the number of treated lesions. Data are presented as mean ± SD.
*p < 0.05 as compared to SFA.

the target vessel location. For the SFA, C is approximately 5%. For the popliteal, C is approximately 8%.

As can be seen from this formula, if all other factors remain the same, the distance between each stent element increases with an increase in length of the stent elements. Likewise, if all other factors remain the same, the distance between each stent element decreases with an increase in the number of elements in the multi-element stent. Similarly, if all other factors remain the same, the distance between each stent element increases with an increase of the maximum percent axial compression of the stent elements at the target vessel location. The approximate relationship between device diameter, length, number of elements and element spacing for devices intended for the superficial femoral artery are shown in Table 4. The approximate relationship between device diameter, length, number of elements and element spacing for devices intended for the popliteal artery are shown in Table 5.

TABLE 4

The approximate relationship between device diameter, length, number of elements and element spacing for devices intended for the superficial femoral artery

| Maximal Deflection (°) | Maximal bend radius (mm) | Maximal axial compression (%) | Length (mm) | Diameter (mm) | Element Length (mm) | Number of Elements | Element Spacing (mm) |
|---|---|---|---|---|---|---|---|
| 8 | 135 | 5 | 20 | 3.0 | 10 | 2 | 1.23 |
| 8 | 135 | 5 | 20 | 4.0 | 10 | 2 | 1.31 |
| 8 | 135 | 5 | 20 | 5.0 | 10 | 2 | 1.39 |
| 8 | 135 | 5 | 20 | 6.0 | 10 | 2 | 1.47 |
| 8 | 135 | 5 | 20 | 8.0 | 10 | 2 | 1.62 |
| 8 | 135 | 5 | 30 | 3.0 | 15 | 2 | 1.73 |
| 8 | 135 | 5 | 30 | 4.0 | 15 | 2 | 1.81 |
| 8 | 135 | 5 | 30 | 5.0 | 15 | 2 | 1.89 |
| 8 | 135 | 5 | 30 | 6.0 | 15 | 2 | 1.97 |
| 8 | 135 | 5 | 30 | 8.0 | 15 | 2 | 2.12 |
| 8 | 135 | 5 | 40 | 3.0 | 20 | 2 | 2.23 |
| 8 | 135 | 5 | 40 | 4.0 | 20 | 2 | 2.31 |
| 8 | 135 | 5 | 40 | 5.0 | 20 | 2 | 2.39 |
| 8 | 135 | 5 | 40 | 6.0 | 20 | 2 | 2.47 |
| 8 | 135 | 5 | 40 | 8.0 | 20 | 2 | 2.62 |
| 8 | 135 | 5 | 60 | 3.0 | 20 | 3 | 1.73 |
| 8 | 135 | 5 | 60 | 4.0 | 20 | 3 | 1.81 |
| 8 | 135 | 5 | 60 | 5.0 | 20 | 3 | 1.89 |
| 8 | 135 | 5 | 60 | 6.0 | 20 | 3 | 1.97 |
| 8 | 135 | 5 | 60 | 8.0 | 20 | 3 | 2.12 |
| 8 | 135 | 5 | 80 | 3.0 | 20 | 4 | 1.57 |
| 8 | 135 | 5 | 80 | 4.0 | 20 | 4 | 1.64 |
| 8 | 135 | 5 | 80 | 5.0 | 20 | 4 | 1.72 |
| 8 | 135 | 5 | 80 | 6.0 | 20 | 4 | 1.80 |
| 8 | 135 | 5 | 80 | 8.0 | 20 | 4 | 1.95 |
| 8 | 135 | 5 | 100 | 3.0 | 20 | 5 | 1.48 |
| 8 | 135 | 5 | 100 | 4.0 | 20 | 5 | 1.56 |
| 8 | 135 | 5 | 100 | 5.0 | 20 | 5 | 1.64 |
| 8 | 135 | 5 | 100 | 6.0 | 20 | 5 | 1.72 |
| 8 | 135 | 5 | 100 | 8.0 | 20 | 5 | 1.87 |

TABLE 5

The approximate relationship between device diameter, length, number of elements and element spacing for devices intended for the popliteal artery

| Maximal Deflection (°) | Maximal bend radius (mm) | Maximal axial compression (%) | Length (mm) | Diameter (mm) | Element Length (mm) | Number of Elements | Element Spacing (mm) |
|---|---|---|---|---|---|---|---|
| 64 | 22 | 8 | 20 | 3.0 | 10 | 2 | 2.32 |
| 64 | 22 | 8 | 20 | 4.0 | 10 | 2 | 2.56 |
| 64 | 22 | 8 | 20 | 5.0 | 10 | 2 | 2.80 |
| 64 | 22 | 8 | 20 | 6.0 | 10 | 2 | 3.04 |
| 64 | 22 | 8 | 20 | 8.0 | 10 | 2 | 3.51 |
| 64 | 22 | 8 | 30 | 3.0 | 10 | 3 | 1.92 |
| 64 | 22 | 8 | 30 | 4.0 | 10 | 3 | 2.16 |
| 64 | 22 | 8 | 30 | 5.0 | 10 | 3 | 2.40 |
| 64 | 22 | 8 | 30 | 6.0 | 10 | 3 | 2.64 |
| 64 | 22 | 8 | 30 | 8.0 | 10 | 3 | 3.11 |
| 64 | 22 | 8 | 40 | 3.0 | 10 | 4 | 1.78 |
| 64 | 22 | 8 | 40 | 4.0 | 10 | 4 | 2.02 |
| 64 | 22 | 8 | 40 | 5.0 | 10 | 4 | 2.26 |
| 64 | 22 | 8 | 40 | 6.0 | 10 | 4 | 2.50 |
| 64 | 22 | 8 | 40 | 8.0 | 10 | 4 | 2.98 |

TABLE 5-continued

The approximate relationship between device diameter, length, number of elements and element spacing for devices intended for the popliteal artery

| Maximal Deflection (°) | Maximal bend radius (mm) | Maximal axial compression (%) | Length (mm) | Diameter (mm) | Element Length (mm) | Number of Elements | Element Spacing (mm) |
|---|---|---|---|---|---|---|---|
| 64 | 22 | 8 | 60 | 3.0 | 10 | 6 | 1.68 |
| 64 | 22 | 8 | 60 | 4.0 | 10 | 6 | 1.92 |
| 64 | 22 | 8 | 60 | 5.0 | 10 | 6 | 2.16 |
| 64 | 22 | 8 | 60 | 6.0 | 10 | 6 | 2.40 |
| 64 | 22 | 8 | 60 | 8.0 | 10 | 6 | 2.87 |
| 64 | 22 | 8 | 80 | 3.0 | 10 | 8 | 1.63 |
| 64 | 22 | 8 | 80 | 4.0 | 10 | 8 | 1.87 |
| 64 | 22 | 8 | 80 | 5.0 | 10 | 8 | 2.11 |
| 64 | 22 | 8 | 80 | 6.0 | 10 | 8 | 2.35 |
| 64 | 22 | 8 | 80 | 8.0 | 10 | 8 | 2.83 |
| 64 | 22 | 8 | 100 | 3.0 | 10 | 10 | 1.61 |
| 64 | 22 | 8 | 100 | 4.0 | 10 | 10 | 1.85 |
| 64 | 22 | 8 | 100 | 5.0 | 10 | 10 | 2.09 |
| 64 | 22 | 8 | 100 | 6.0 | 10 | 10 | 2.33 |
| 64 | 22 | 8 | 100 | 8.0 | 10 | 10 | 2.80 |

The stents described herein may be formed from various different materials. In an embodiment, stents may be formed a polymer. In various alternative embodiments, the stent or stent element may be made from any suitable bioresorbable material such that it will dissolve non-toxically in the human body, such as but not limited to poly(L-lactic acid) (PLLA), polyglycolic acid (PGA), poly(iodinated desaminotyrosyl-tyrosine ethyl ester) carbonate, or the like. In one embodiment, at least two of the elements comprise different materials. For example, the outer elements may comprise of a faster degrading bioresorbable material than the inner elements of a bioresorbable, multi-element stent.

In alternative embodiments, any suitable polymer may be used to construct the stent. The term "polymer" is intended to include a product of a polymerization reaction inclusive of homopolymers, copolymers, terpolymers, etc., whether natural or synthetic, including random, alternating, block, graft, branched, cross-linked, blends, compositions of blends and variations thereof. The polymer may be in true solution, saturated, or suspended as particles or supersaturated in the beneficial agent. The polymer can be biocompatible, or biodegradable. For purpose of illustration and not limitation, the polymeric material may include, but is not limited to, poly(D-lactic acid) (PDLA), poly(D,L-lactic acid) (PDLLA), poly(iodinated desamino tyrosyl-tyrosine ethyl ester) carbonate, poly(lactic-co-glycolic acid) (PLGA), salicylate based polymer, semicrystalline polylactide, phosphorylcholine, polycaprolactone (PCL), poly-D,L-lactic acid, poly-L-lactic acid, poly(lactideco-glycolide), poly(hydroxybutyrate), poly(hydroxybutyrate-co-valerate), polydioxanone (PDS), polyorthoester, polyanhydride, poly(glycolic acid), poly(glycolic acid-co-trimethylene carbonate), polyphosphoester, polyphosphoester urethane, poly(amino acids), cyanoacrylates, poly(trimethylene carbonate), poly (iminocarbonate), polyalkylene oxalates, polyphosphazenes, polyiminocarbonates, and aliphatic polycarbonates, fibrin, fibrinogen, cellulose, starch, collagen, polyurethane including polycarbonate urethanes, polyethylene, polyethylene terephthalate, ethylene vinyl acetate, ethylene vinyl alcohol, silicone including polysiloxanes and substituted polysiloxanes, polyethylene oxide, polybutylene terephthalate-co-PEG, PCL-co-PEG, PLA-co-PEG, PLLA-co-PCL, polyacrylates, polyvinyl pyrrolidone, polyacrylamide, and combinations thereof. Non-limiting examples of other suitable polymers include thermoplastic elastomers in general, polyolefin elastomers, EPDM rubbers and polyamide elastomers, and biostable plastic material including acrylic polymers, and its derivatives, nylon, polyesters and expoxies. In some embodiments, the stent may include one or more coatings, with materials like poly(D,L-lactic acid) (PDLLA). These materials are merely examples, however, and should not be seen as limiting the scope of the invention.

Stent elements may comprise various shapes and configurations. Some or all of the stent elements may comprise closed-cell structures formed by intersecting struts. Closed-cell structures may comprise diamond, square, rectangular, parallelogrammatic, triangular, pentagonal, hexagonal, heptagonal, octagonal, clover, lobular, circular, elliptical, and/or ovoid geometries. Closed-cells may also comprise slotted shapes such as H-shaped slots, I-shaped slots, J-shaped slots, and the like. Additionally or alternatively, stent may comprise open cell structures such as spiral structures, serpentine structures, zigzags structures, etc. Strut intersections may form pointed, perpendicular, rounded, bullnosed, flat, beveled, and/or chamfered cell corners. In an embodiment, stent may comprise multiple different cells having different cell shapes, orientations, and/or sizes. Various cell structures have been described in PCT International Application Number PCT/US16/20743, entitled "MULTI-ELEMENT BIORESORBABLE INTRAVASCULAR STENT", the full disclosure of which is herein incorporated by reference.

Returning to FIG. 2B, in this exemplary embodiment, the stent elements 201 have a diamond shaped closed-cell pattern. Elements 201 comprise intermixed diamond shaped closed cells 204, 205. Diamond shaped cells 204 may be aligned in the longitudinal and/or the circumferential directions in a repeating pattern. Similarly, diamond shaped cells 205 may be aligned in the longitudinal and/or the circumferential directions in a repeating pattern. Additionally or alternatively, diamond shaped cells 204 and diamond shaped cells 205 may be helically aligned in an alternating pattern. In an embodiment, diamond shaped cells 204 and diamond shaped cells 205 are circumferentially offset. Additionally, diamond shaped cells 205 may be formed at a central location between four adjacent diamond shaped cells 204. The width of struts 206 between two corners of longitudinally aligned diamond shaped cells 204 are larger than the width of struts 207 between two corners of longitudinally aligned diamond shaped cells 205.

In contrast to most balloon-expandable stent patterns which are designed to minimize foreshortening upon stent expansion, various patterns described herein are specifically designed to shorten upon expansion, such that the length of deployed element is considerably less than the length of the element when crimped. Heretofore felt to be an undesirable property of intravascular stents, the patterns described herein are actually intended to shorten to create the final result of discontinuity of the fully deployed device within the vessel.

One embodiment of a stent pattern designed to shorten upon expansion is shown in shown in FIGS. 7A-7D. The structure of a stent pattern may be designed for maximal radial force and stiffness which will lengthen when crimped and foreshorten when expanded. The stent elements 701 have a diamond shaped closed-cell pattern with relatively thick strut widths and obliquely-angled links. Elements 701 comprise diamond shaped closed cells 704. Elements 701 may comprise wide struts 706 of 225 microns or larger. Elements 701 may similarly comprise thick struts 706 of 225 microns or larger. In an embodiment, elements 701 comprise struts 706 with a width and/or thickness of approximately 250 microns. The width and/or the height of struts 706 between two corners of diamond shaped cells 704 may be larger or smaller than the width and/or height of struts 706 forming the sides of diamond shaped cells 704.

FIGS. 8A-8D show cell views of patterns of stent elements that shorten upon expansion. Individual cell patterns of absorbable intravascular stents designed for maximal radial force and stiffness which will lengthen when crimped and foreshorten when expanded. Stent elements may have diamond-shaped, closed cell structure with relatively thick strut widths and obliquely-angled links.

Figure 9:
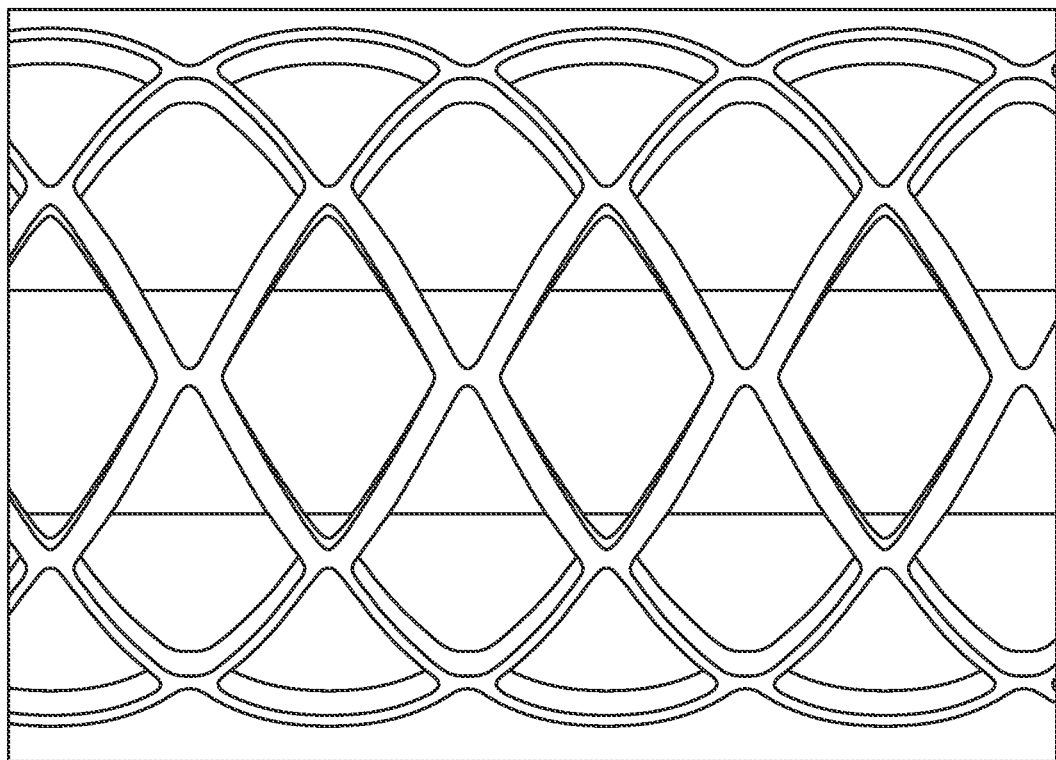
FIG. 9 shows a laser cut stent.
Figure 10A:
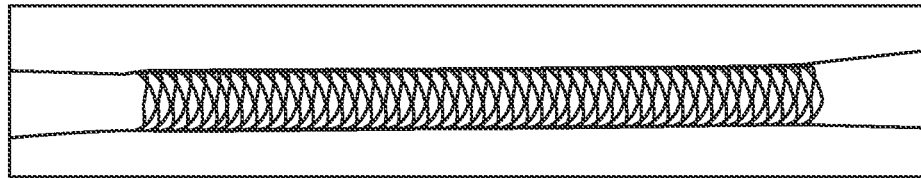
FIGS. 10A-10E show a multi-element stent mounted on an angioplasty balloon.
Figure 10B:
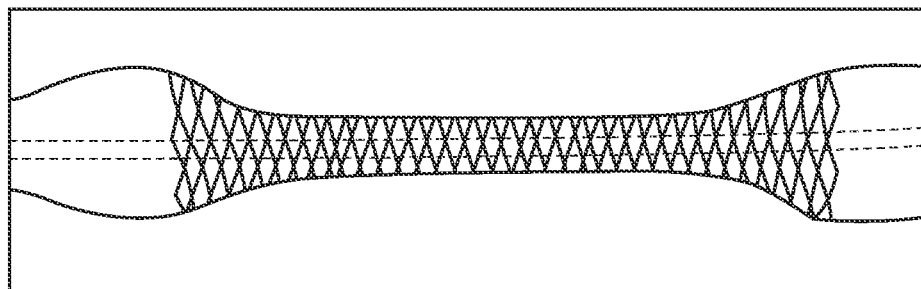
Figure 10C:
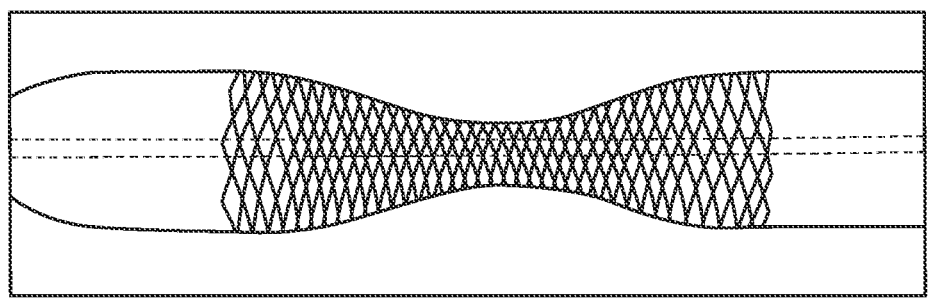
Figure 10D:
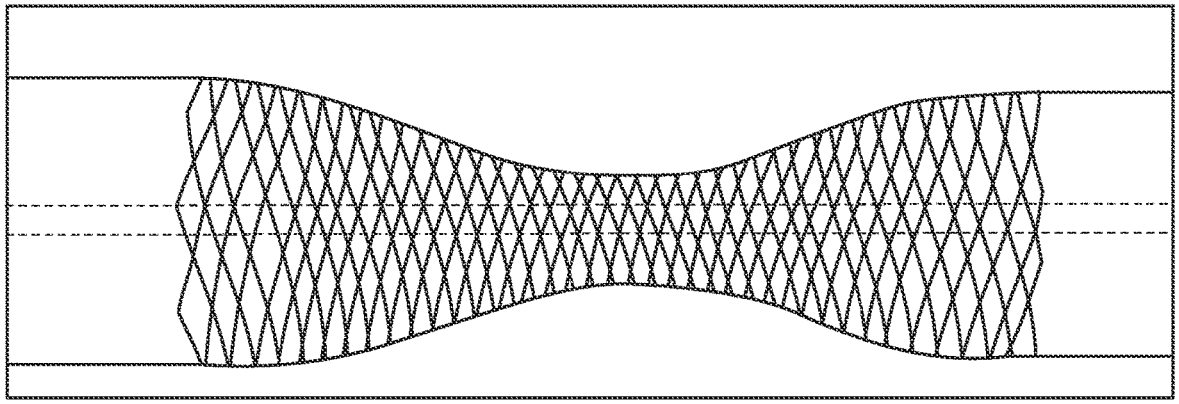
Figure 10E:
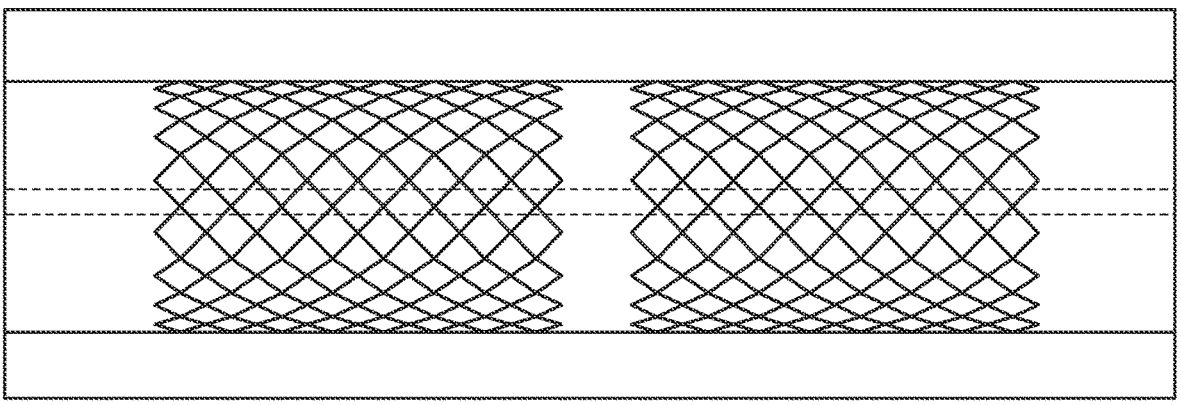
Figure 12A:
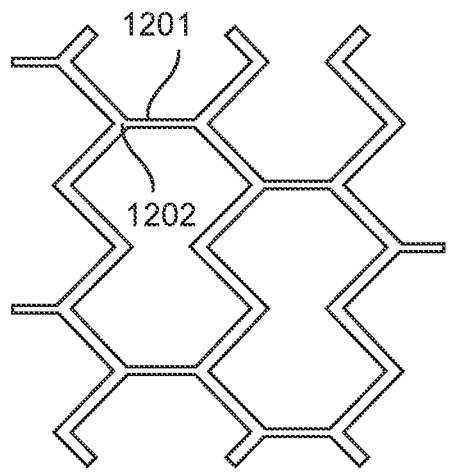
FIGS. 12A-12D show cell patterns with various connector configurations.
Figure 12B:
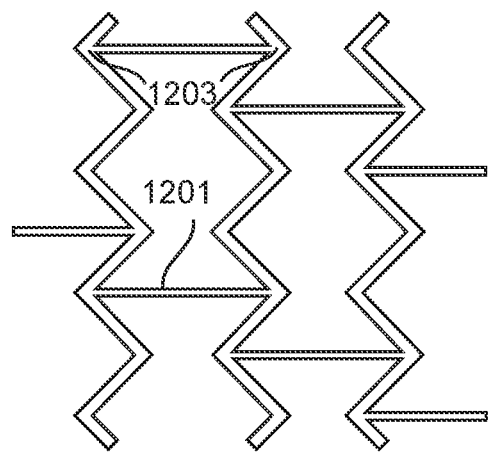
Figure 12C:
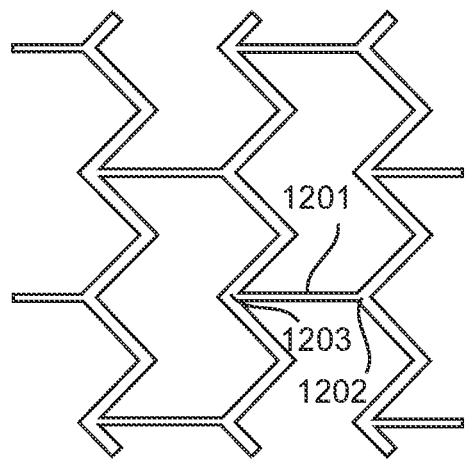
Figure 12D:
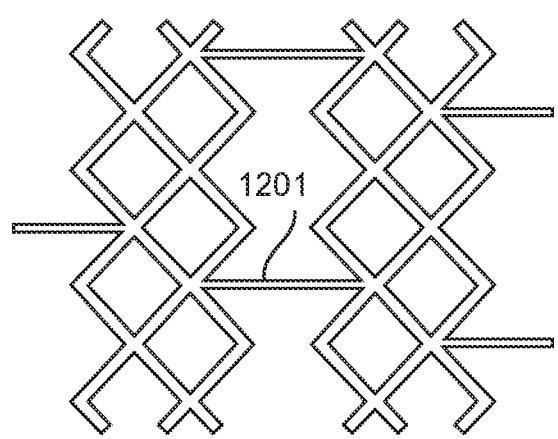

An example of an actual laser-cut stent designed herein is shown in FIG. 9. FIGS. 10A-10E show two such segments mounted on a standard angioplasty balloon. FIG. 10A shows two segments crimped on an angioplasty balloon. The segments were applied with an intervening space which was eliminated as the stents lengthened during crimping. To the naked eye, the device appears as a single, continuous stent. However, when then balloon is inflated the two rigid stent segments shorten so as to create an intervening space between them (FIGS. 10B-10E). As the segments are rigid, the intervening space allows for the artery to bend with normal skeletal motion.

There are several parameters that may be manipulated to engineer the desired spacing between elements. Examples of seven of these parameters are provided here.

Parameter 1: Stent Pattern

The stent pattern generally affects the amount of foreshortening a stent undergoes during expansion. The more a given pattern foreshortens, the larger a space is created between the elements. Many features of the stent pattern can be manipulated to achieve the desired amount of foreshortening and inter-element spacing.

One feature that can be manipulated is the change of angle that the struts undergo during expansion. The change of angle can be seen in FIGS. 11A-11F. FIGS. 11A-11F show finite element analysis (FEA) of a bioresorbable polymer stent cell that lengthens upon crimping and shortens upon expansion. The stress scale is shown at the left. FIGS. 11A-11F show progressive crimping of a single cell 1104. Note the maximal stress of 156 mises even when fully crimped (FIG. 11F) demonstrates that the device can be effectively crimped without undue strain or fracture. In 11F, the struts are in the crimped configuration prior to expansion and each strut is essentially horizontal. In 11A, the struts are in the fully expanded configuration and each strut has rotated from a horizontal orientation to a more upright orientation. The larger this change of angle, the more the pattern will foreshorten in the case of a closed cell pattern. Changing the length of struts or the number of cells circumferentially around the stent element can affect the change in angle.

In the case of an open cell pattern, a larger change of angle of the struts during expansion may increase, decrease, or not affect foreshortening depending on the configuration of the connectors between rings. FIGS. 12A-12D show cell patterns with various connector configurations. If connectors 1201 connect the peaks 1202 of one ring to the peaks 1202 of another ring (FIG. 12A), that portion of the pattern will react like a closed cell pattern and increased change of angle of the struts will cause increased foreshortening and increase inter-element spacing. If the connectors 1201 connect the valleys 1203 of one ring to the valleys 1203 of another (FIG. 12B), increased change of the angle of the struts will cause lengthening upon expansion and that portion of the pattern will cause decreased inter-element spacing. If the connectors 1201 connect the valleys 1203 of one ring to the peaks 1202 of another (FIG. 12C), increased change of the angle of the struts will not affect the length of the stent during expansion.

The various connector configurations mentioned above may be used combined with each other and/or with a closed cell pattern to manipulate the amount of foreshortening and the size of the inter-element spacing. For example, the pattern shown in FIG. 12D combines one ring of open cell pattern with every two rings of a closed cell pattern. The particular connector 1201 configuration in the open cell portion contributes lengthening upon expansion while the closed cell portion foreshortens upon expansion. The lengthening partially offsets the foreshortening thus leading to a smaller amount of foreshortening than what would result from using only a closed cell pattern.

Parameter 2: Element Length:

Given a certain amount of foreshortening per unit length of a stent element, the amount of foreshortening in absolute terms is proportional to the length of the element. Since the inter-element spacing is determined by the amount of foreshortening, it is also proportional to the element length.

Parameter 3: Deployment Diameter:

For a stent element that foreshortens during deployment and creates a space to the next element, the foreshortening and the space created both become larger as the diameter to which the element is expanded becomes larger.

Parameter 4: Crimped Spacing:

The spacing between the elements after deployment may be directly manipulated by changing the spacing before deployment when the elements are crimped onto the balloon. In the example device shown in FIGS. 10A-10F, the elements are crimped such that they are touching and all of the inter-element space is created by foreshortening and/or movement of the elements. However, this is not a requirement. The elements may also be crimped with pre-existing spacing that is increased during deployment. In an embodiment, elements may be crimped with a pre-existing space of 1 mm or less.

Parameter 5: Stent Material:

The stent material may impact the amount of space created in two ways. First, because different materials can undergo differing amounts of strain before fracturing and different stent patterns cause the material to undergo different amounts of strain during deployment, the material used impacts the design of the stent pattern. Second, even when the same stent pattern is used, different materials may react differently to both the crimping and deployment processes thus resulting is different amounts of foreshortening and influencing the size of the inter-element spaces.

Parameter 6: Crimping Process Variables:

Balloon expandable bioresorbable stents may be first manufactured at a diameter approximating the eventual deployment diameter and then crimped or collapsed into a smaller diameter onto a balloon via a crimping process. A stent element that foreshortens during deployment, lengthens during the crimping process. The amount of lengthening and the deformation of the stent pattern that occur during crimping can both be affected by several variables of the crimping process. The amount of lengthening that a stent element undergoes during crimping, in turn, affects the amount that the element foreshortens during deployment and the size of the inter-element spaces created. The variables that affect lengthening during the crimping process include the temperature at which crimping is performed, the time over which crimping takes place, the presence or absence of an inflated balloon during portions of the crimping process and the pressure of the balloon. For example, if a higher temperature is used during crimping, the material may become softer and the struts of the stent may deform more during crimping leading to a lower amount of lengthening which in turn would lead to less foreshortening during deployment.

Parameter 7: Balloon Material:

The material of the balloon used to deploy the stent can affect the size of the inter-elements spaces because different balloon materials produce different amounts of friction between the balloon and the stent. Thus differing balloon materials may allow more or less movement of the whole stent element or just portions of the element relative to the balloon. This can affect the size of the inter-element spaces in two ways. First, the movement allowed affects the amount of lengthening that occurs in the elements during crimping and the amount of foreshortening that occurs during deployment. Second, the movement allowed may affect movement of the entire element during deployment. For example, if a space opens up between two elements during deployment, the elements may slide away from each other increasing the size of the space. The amount that the elements slide apart would be affected by the material of the balloon.

Figure 13A:
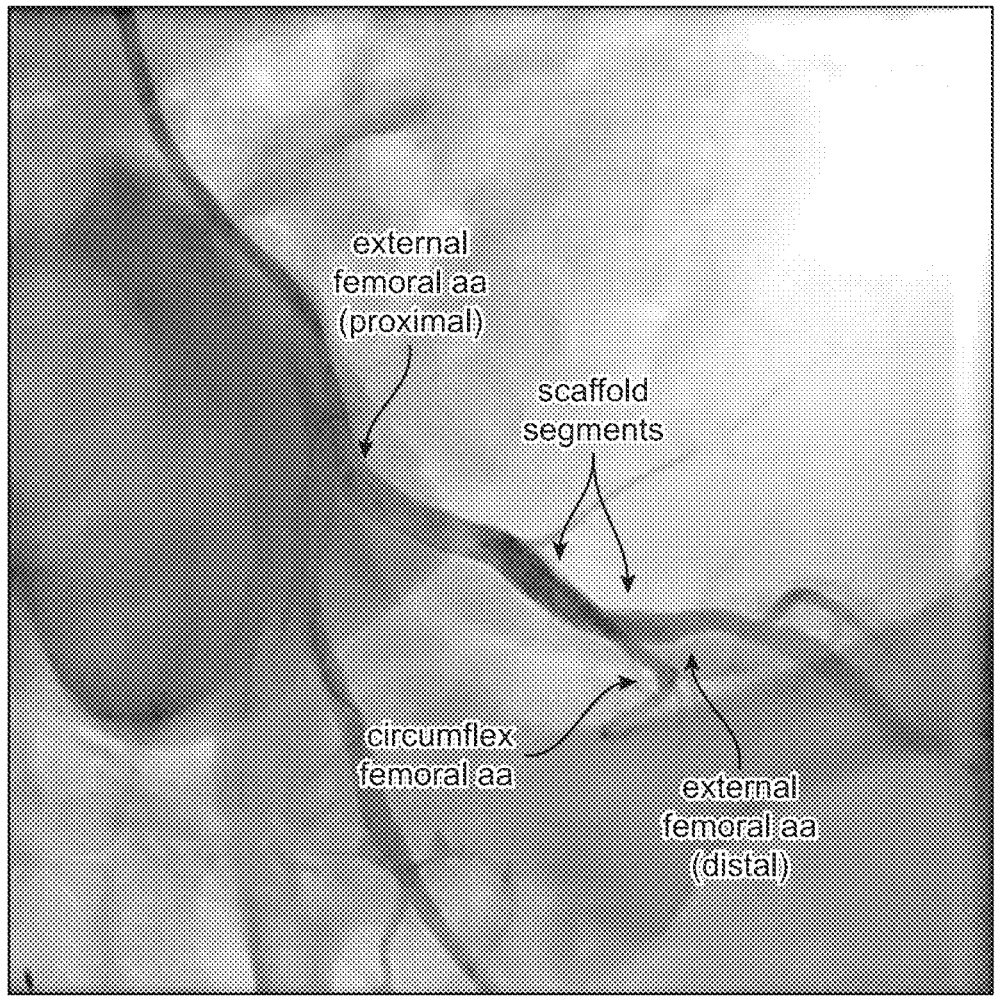
FIGS. 13A-13C show a two-segment device deployed in the left iliofemoral artery.
Figure 13B:
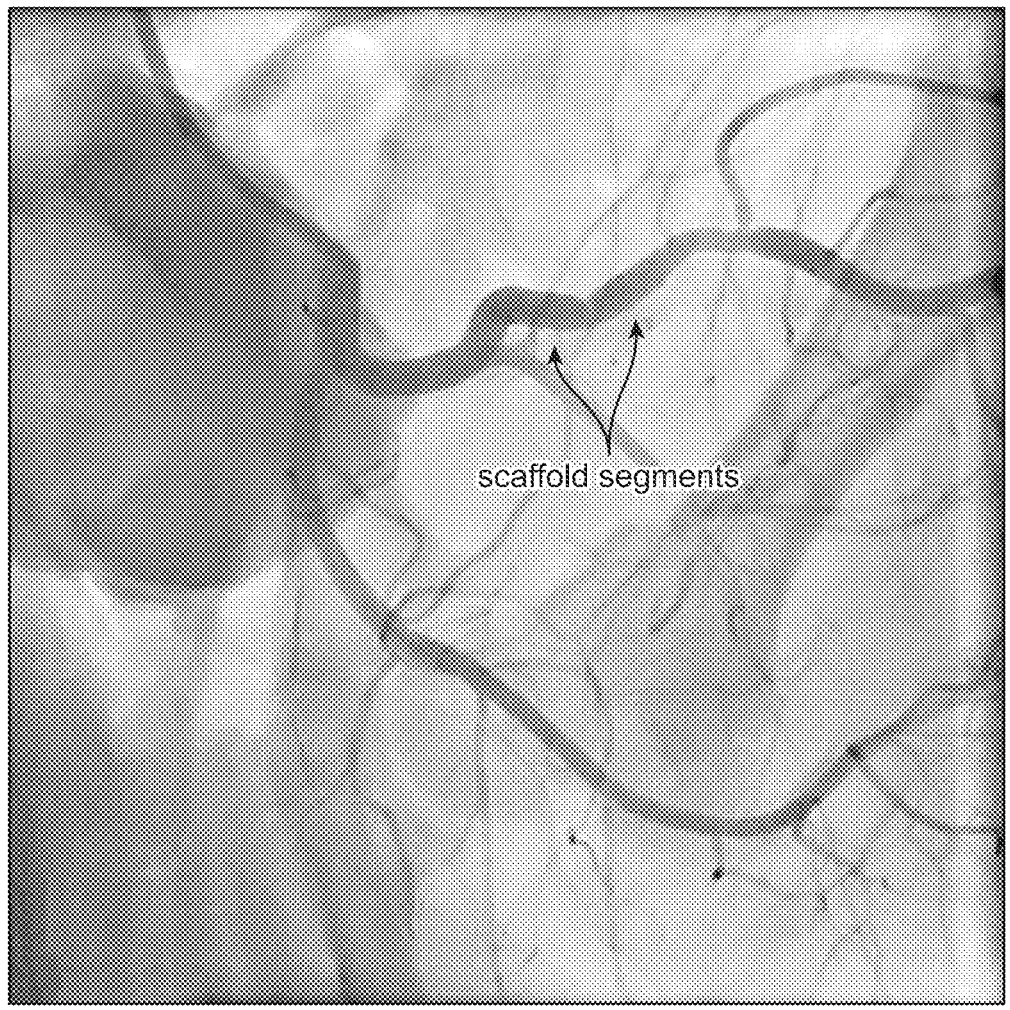
Figure 13C:
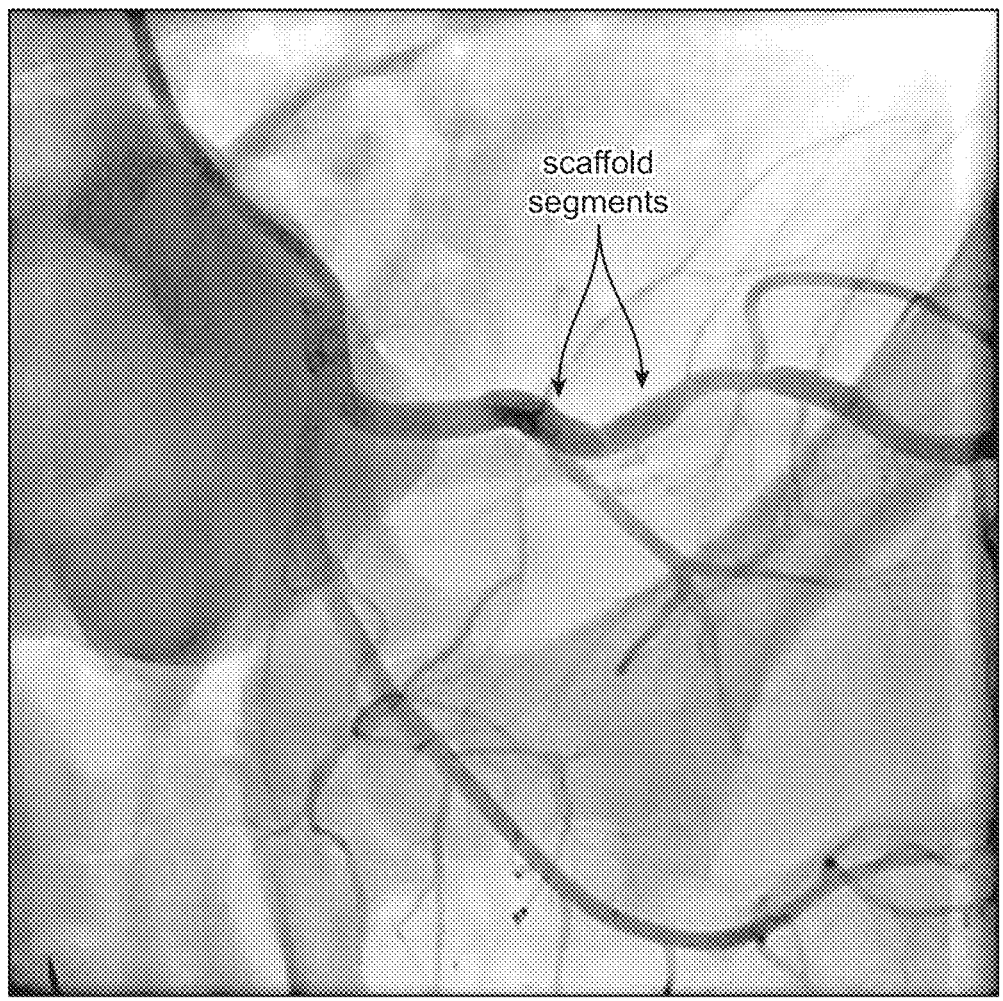
Figure 14:
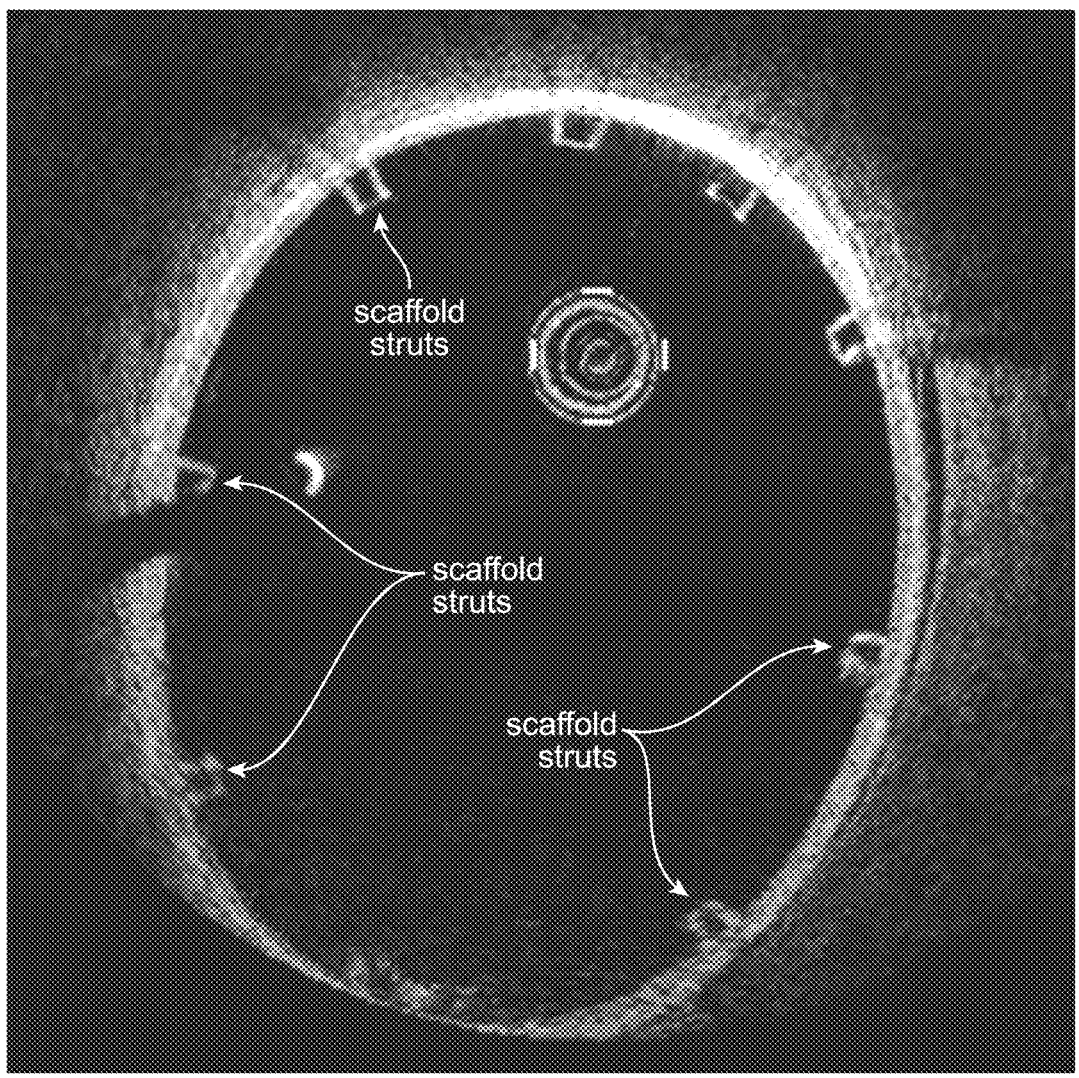
FIG. 14 shows an optical coherence tomographic (OCT) image of a deployed bioresorbable stent in the porcine iliofemoral artery.

An embodiment of the device was tested acutely by implantation into experimental animals. Domestic farm pigs were anesthetized with ketamine, azaperone and atropine administered intramuscularly. Via surgical exposure, a sheath was placed in the right common carotid artery and wire access of the left iliofemoral arterial system secured under fluoroscopic control. A two-segment device was deployed in the left iliofemoral artery as shown in FIGS. 13A-13C. In FIG. 13A, the left hind limb is extended. FIG. 13B shows the animal's hind limb flexed to simulate flexion of the human superficial femoral artery. The artery bends in the intervening space between the two stents; the scaffold segments themselves remain rigid and straight. FIG. 13C shows extreme, non-physiologic flexion of the hind limb. The stented artery remained patent by bending within the intervening space between the two rigid stents Following deployment, Optimal Coherence Tomographic (OCT) imaging was performed using the Illumien Optis imaging system (Abbott Laboratories, Abbott Park, Ill.). The OCT catheter was advanced beyond the device, into the distal vessel, and pulled back to a point proximal to the device. An optical coherence tomographic (OCT) image of the deployed bioresorbable stent in the porcine iliofemoral artery is shown in FIG. 14. Because of the high radial strength of the device, all scaffold struts are completely opposed to the arterial wall.

Figure 15A:
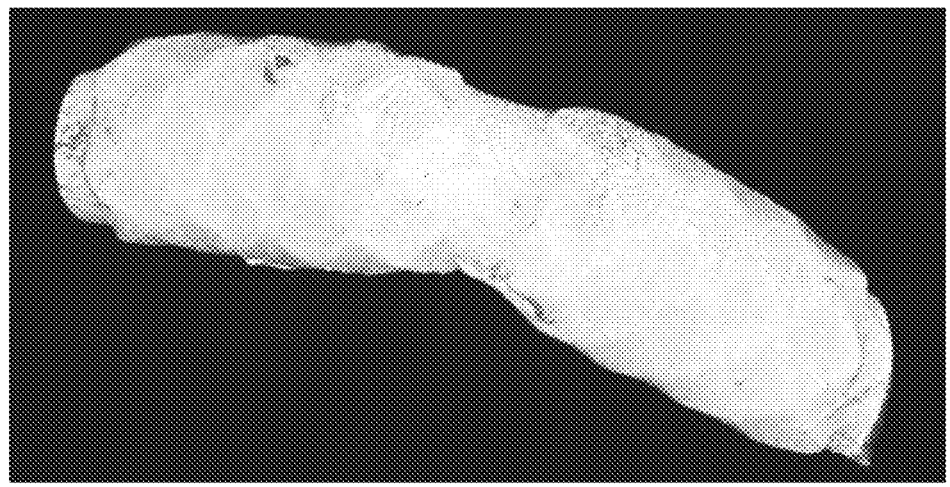
FIGS. 15A-C show Micro-CT images of a scaffolded artery.
Figure 15B:
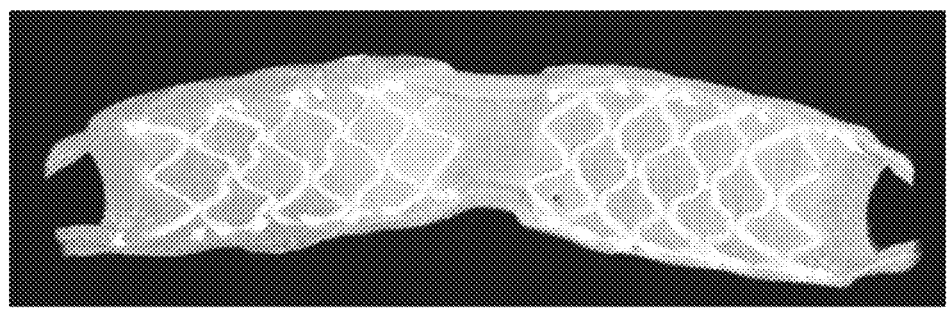
Figure 15C:
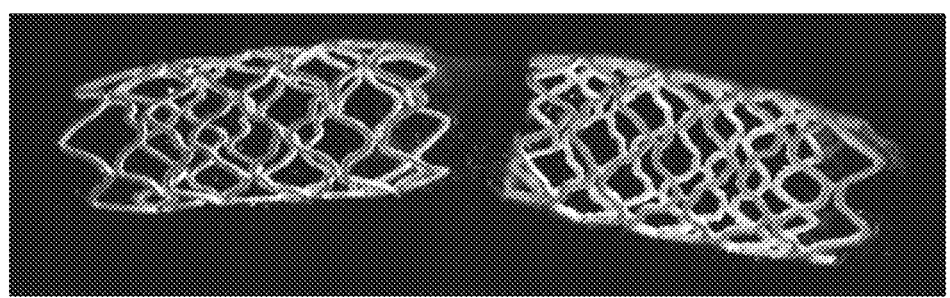

Following deployment and imaging, the animal was euthanized by a lethal injection of saturated potassium chloride while maintaining deep anesthesia. The lower body was perfused with lactated Ringer's solution then neutral buffered formalin. The scaffolded artery was excised and treated with graded alcohol then scanned using a Nikon XT H 225 micro-computed tomograph. Micro-CT images are shown in FIGS. 15A-C. The scaffolded artery is shown intact in FIG. 15A. Subtraction of the anterior arterial wall is shown in FIG. 15B. FIG. 15C shows subtraction of the entire arterial wall. The devices shortened upon expansion creating an intervening space about which the supple artery has hinged.

Figures 16A, 16B:
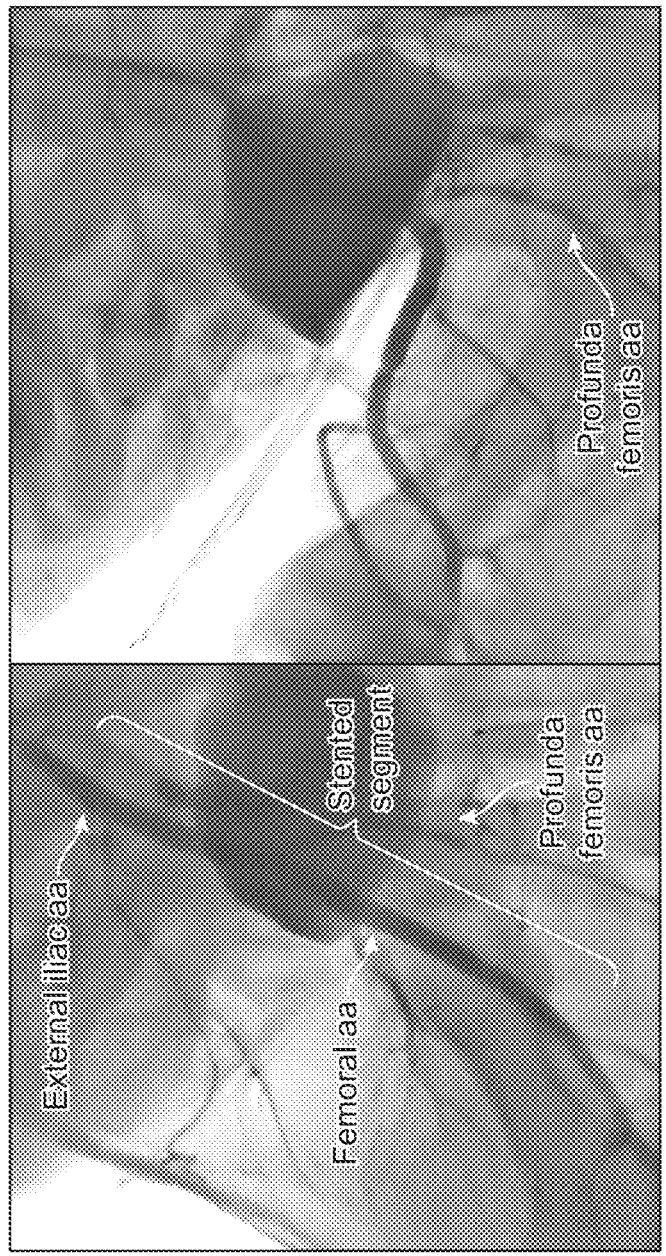
FIGS. 16A and 16B show eight serial balloon-expandable stent segments implanted the full length of a porcine iliofemoral artery.

Eight serial balloon-expandable stent segments were implanted the full length of the porcine iliofemoral artery. The results are shown in FIGS. 16A and 16B. A total of eight segments were implanted in approximately 12 cm of total iliofemoral arterial length. FIG. 16A shows the animal's hind limb extended. Aortic injection demonstrates wide patency of the stented artery. Patency is redemonstrated even when the hind limb is manually flexed (FIG. 16B). Even though the artery has been treated with multiple, serial, rigid stents, its capacity for motion is preserved by the intervening spaces created by stent shortening.

The device described herein may include incorporation of a therapeutic drug on one or more of the stent elements of the multi-element stent. In one embodiment, the therapeutic drug may be intended to prevent or attenuate pathologic consequences of intraluminal intervention such as inflammation, cell dysfunction, cell activation, cell proliferation, neointimal formation, thickening, late atherosclerotic change and/or thrombosis. Any suitable therapeutic agent (or "drug") may be incorporated into, coated on, or otherwise attached to the stent, in various embodiments. Examples of such therapeutic agents include, but are not limited to, antithrombotics, anticoagulants, antiplatelet agents, anti-lipid agents, thrombolytics, antiproliferatives, anti-inflammatories, agents that inhibit hyperplasia, smooth muscle cell inhibitors, antibiotics, growth factor inhibitors, cell adhesion inhibitors, cell adhesion promoters, antimitotics, antifibrins, antioxidants, anti-neoplastics, agents that promote endothelial cell recovery, matrix metalloproteinase inhibitors, anti-metabolites, antiallergic substances, viral vectors, nucleic acids, monoclonal antibodies, inhibitors of tyrosine kinase, antisense compounds, oligonucleotides, cell permeation enhancers, hypoglycemic agents, hypolipidemic agents, proteins, nucleic acids, agents useful for erythropoiesis stimulation, angiogenesis agents, anti-ulcer/anti-reflux agents, and anti-nauseants/anti-emetics, PPAR alpha agonists such as fenofibrate, PPAR-gamma agonists selected such as rosiglitazaone and pioglitazone, sodium heparin, LMW heparins, heparoids, hirudin, argatroban, forskolin, vapriprost, prostacyclin and prostacylin analogues, dextran, D-phe-pro-arg-chloromethylketone (synthetic anti-thrombin), glycoprotein IIb/IIIa (platelet membrane receptor antagonist antibody), recombinant hirudin, thrombin inhibitors, indomethacin, phenyl salicylate, beta-estradiol, vinblastine, ABT-627 (astrasentan), testosterone, progesterone, paclitaxel, methotrexate, fotemusine, RPR-101511A, cyclosporine A, vincristine, carvediol, vindesine, dipyridamole, methotrexate, folic acid, thrombospondin mimetics, estradiol, dexamethasone, metrizamide, iopamidol, iohexol, iopromide, iobitridol, iomeprol, iopentol, ioversol, ioxilan, iodixanol, and iotrolan, antisense compounds, inhibitors of smooth muscle cell proliferation, lipid-lowering agents, radiopaque agents, antineoplastics, HMG CoA reductase inhibitors such as lovastatin, atorvastatin, simvastatin, pravastatin, cerivastatin and fluvastatin, and combinations thereof.

Examples of antithrombotics, anticoagulants, antiplatelet agents, and thrombolytics include, but are not limited to, sodium heparin, unfractionated heparin, low molecular weight heparins, such as dalteparin, enoxaparin, nadroparin, reviparin, ardoparin and certaparin, heparinoids, hirudin, argatroban, forskolin, vapriprost, prostacyclin and prostacylin analogues, dextran, D-phe-pro-arg-chloromethylketone (synthetic antithrombin), dipyridamole, glycoprotein IIb/IIIa (platelet membrane receptor antagonist antibody), recombinant hirudin, and thrombin inhibitors such as bivalirudin, thrombin inhibitors, and thrombolytic agents, such as urokinase, recombinant urokinase, pro-urokinase, tissue plasminogen activator, ateplase and tenecteplase.

Examples of cytostatic or antiproliferative agents include, but are not limited to, rapamycin and its analogs, including everolimus, zotarolimus, tacrolimus, novolimus, and pimecrolimus, angiopeptin, angiotensin converting enzyme inhibitors, such as captopril, cilazapril or lisinopril, calcium channel blockers, such as nifedipine, amlodipine, cilnidipine, lercanidipine, benidipine, trifluperazine, diltiazem and verapamil, fibroblast growth factor antagonists, fish oil (omega 3-fatty acid), histamine antagonists, lovastatin, topoisomerase inhibitors, such as etoposide and topotecan, as well as antiestrogens such as tamoxifen.

Examples of anti-inflammatory agents include, but are not limited to, colchicine and glucocorticoids, such as betamethasone, cortisone, dexamethasone, budesonide, prednisolone, methylprednisolone and hydrocortisone. Non-steroidal anti-inflammatory agents include, but are not limited to, flurbiprofen, ibuprofen, ketoprofen, fenoprofen, naproxen, diclofenac, diflunisal, acetaminophen, indomethacin, sulindac, etodolac, diclofenac, ketorolac, meclofenamic acid, piroxicam and phenylbutazone.

Examples of antineoplastic agents include, but are not limited to, alkylating agents including altretamine, bendamucine, carboplatin, carmustine, cisplatin, cyclophosphamide, fotemustine, ifosfamide, lomustine, nimustine, prednimustine, and treosulfin, antimitotics, including vincristine, vinblastine, paclitaxel, docetaxel, antimetabolites including methotrexate, mercaptopurine, pentostatin, trimetrexate, gemcitabine, azathioprine, and fluorouracil, antibiotics, such as doxorubicin hydrochloride and mitomycin, and agents that promote endothelial cell recovery such as estradiol.

Antiallergic agents include, but are not limited to, permirolast potassium nitroprusside, phosphodiesterase inhibitors, prostaglandin inhibitors, suramin, serotonin blockers, steroids, thioprotease inhibitors, triazolopyrimidine, and nitric oxide.

The beneficial agent may include a solvent. The solvent may be any single solvent or a combination of solvents. For purpose of illustration and not limitation, examples of suitable solvents include water, aliphatic hydrocarbons, aromatic hydrocarbons, alcohols, ketones, dimethyl sulfoxide, tetrahydrofuran, dihydrofuran, dimethylacetamide, acetates, and combinations thereof.

Stents may be manufactured using an additive or a subtractive. In any of the described embodiments, stents or stent elements may be manufactured as a sheet and wrapped into cylindrical form. Alternatively, stents or stent elements may be manufactured in cylindrical form using an additive manufacturing process. In an embodiment, stents may be formed by extruding a material into a cylindrical tubing. In some embodiments, a longer stent element, may be formed during the manufacturing process and then cut into smaller stent elements/elements to provide a multi-element stent. In an embodiment, stent tubing may be laser cut with a pattern to form a stent element.

Figure 17:
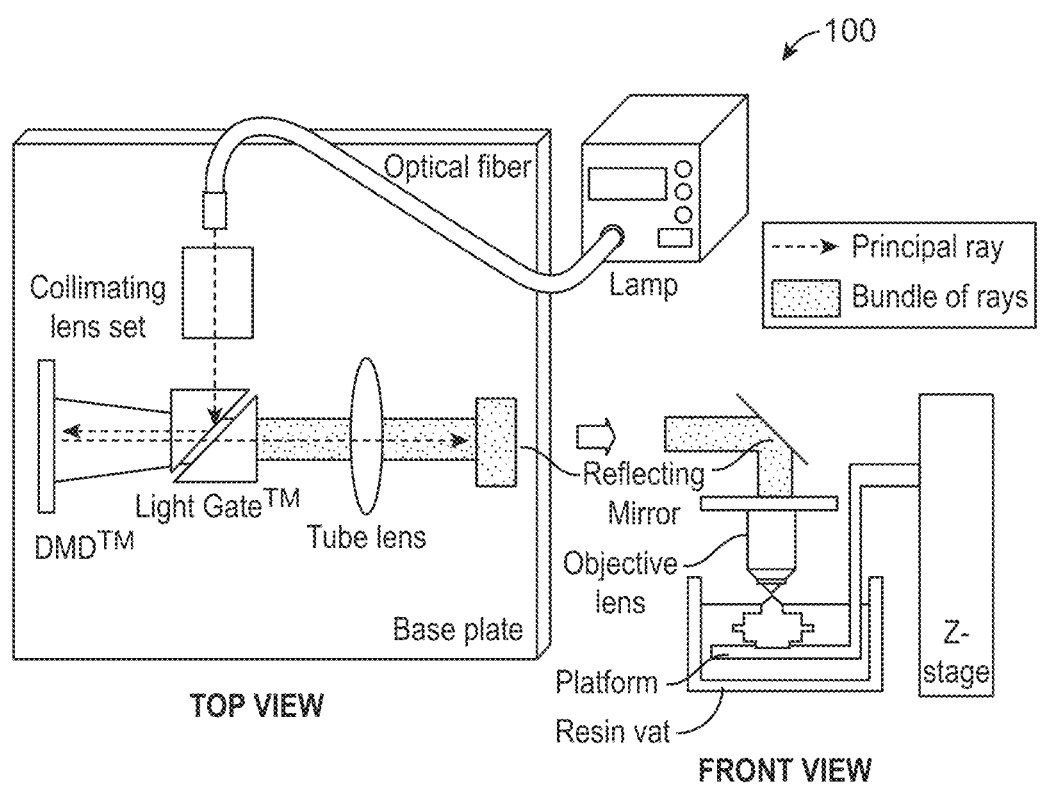
FIG. 17 is a schematic diagram of a micro-stereolithograph used to create a stent, according to one embodiment.

Referring now to FIG. 17, in one embodiment, stents may be manufactured using a micro-stereolithography system 100 (or "3D printing system"). Several examples of currently available systems that might be used in various embodiments include, but are not limited to: MakiBox A6, Makible Limited, Hong Kong; CubeX, 3D Systems, Inc., Circle Rock Hill, S.C.; and 3D-Bioplotter, (EnvisionTEC GmbH, Gladbeck, Germany).

The micro-stereolithography system may include an illuminator, a dynamic pattern generator, an image-former and a Z-stage. The illuminator may include a light source, a filter, an electric shutter, a collimating lens and a reflecting mirror that projects a uniformly intense light on a digital mirror device (DMD), which generates a dynamic mask. FIG. 10 shows some of these components of one embodiment of the micro-stereolithography system 100, including a DMD board, Z-stage, lamp, platform, resin vat and an objective lens. The details of 3D printing/micro-stereolithography systems and other additive manufacturing systems will not be described here, since they are well known in the art. However, according to various embodiments, any additive manufacturing system or process, whether currently known or hereafter developed, may potentially be used to fabricate stents within the scope of the present invention. In other words, the scope of the invention is not limited to any particular additive manufacturing system or process.

In one embodiment, the system 100 may be configured to fabricate stents using dynamic mask projection micro-stereolithography. In one embodiment, the fabrication method may include first producing 3D microstructural scaffolds by slicing a 3D model with a computer program and solidifying and stacking images layer by layer in the system. In one embodiment, the reflecting mirror of the system is used to project a uniformly intense light on the DMD, which generates a dynamic mask. The dynamic pattern generator creates an image of the sliced section of the fabrication model by producing a black-and-white region similar to the mask. Finally, to stack the images, a resolution Z-stage moves up and down to refresh the resin surface for the next curing. The Z-stage build subsystem, in one embodiment, has a resolution of about 100 nm and includes a platform for attaching a substrate, a vat for containing the polymer liquid solution, and a hot plate for controlling the temperature of the solution. The Z-stage makes a new solution surface with the desired layer thickness by moving downward deeply, moving upward to the predetermined position, and then waiting for a certain time for the solution to be evenly distributed.

Although particular embodiments have been shown and described, they are not intended to limit the invention. Various changes and modifications may be made to any of the embodiments, without departing from the spirit and scope of the invention. The invention is intended to cover alternatives, modifications, and equivalents.

What is claimed is:

1. A device for placement within a blood vessel to maintain or enhance blood flow through the blood vessel, the device comprising:
   multiple, balloon-expandable, bioresorbable, vascular stent elements configured to be implanted in the blood vessel as a multi-element stent;

wherein the stent elements are configured to be positioned serially along a longitudinal length of a balloon with a space between the stent elements in an unexpanded state of 1 mm or less;

wherein the stent elements are configured to shorten upon balloon expansion to an expanded state at a target vessel location to create a space between the stent elements in the expanded state such that the stent elements do not touch one another at the target vessel location during skeletal movement;

wherein the multi-element stent is configured to be radially rigid and longitudinally flexible after implantation at the target vessel location;

wherein a cell pattern of the stent elements is configured to shorten the stent elements upon expansion and provide the space between the stent elements in the expanded state; and wherein the stent elements comprise one or more shortening sections configured to shorten upon expansion to the expanded state and one or more lengthening sections configured to lengthen upon expansion to the expanded state.

2. The device of claim 1, wherein the one or more shortening sections comprise closed cells.

3. The device of claim 1, wherein the one or more shortening sections comprise open cells with one or more struts connecting one or more peaks of a first ring to one or more peaks of a second ring.

4. The device of claim 1, wherein the one or more lengthening sections comprise open cells with one or more struts connecting one or more valleys of a first ring to one or more valleys of a second ring.

5. The device of claim 1, further comprising a therapeutic drug, wherein the therapeutic drug prevents or attenuates inflammation, cell dysfunction, cell activation, cell proliferation, neointimal formation, thickening, late atherosclerotic change or thrombosis.

6. The device of claim 1, wherein the stent elements are formed from a bioresorbable polymer material, and wherein the bioresorbable polymer material comprises poly(L-lactic acid) (PLLA), poly(D-lactic acid) (PDLA), poly(D,L-lactic acid) (PDLLA), semicrystalline polylactide, polyglycolic acid (PGA), poly(lactic-co-glycolic acid) (PLGA), poly(iodinated desamino tyrosyl-tyrosine ethyl ester) carbonate, polycaprolactone (PCL), salicylate based polymer, polydioxanone (PDS), poly(hydroxybutyrate), poly(hydroxybutyrate-co-valerate), polyorthoester, polyanhydride, poly(glycolic acid-co-trimethylene carbonate), poly(iodinated desaminotyrosyl-tyrosine ethyl ester) carbonate, polyphosphoester, polyphosphoester urethane, poly(amino acids), cyanoacrylates, poly(trimethylene carbonate), poly(iminocarbonate), polyalkylene oxalates, polyphosphazenes, polyiminocarbonates, and aliphatic polycarbonates, fibrin, fibrinogen, cellulose, starch, collagen, polyurethane including polycarbonate urethanes, polyethylene, polyethylene terephthalate, ethylene vinyl acetate, ethylene vinyl alcohol, silicone including polysiloxanes and substituted polysiloxanes, polyethylene oxide, polybutylene terephthalate-co-PEG, PCL-co-PEG, PLA-co-PEG, PLLA-co-PCL, polyacrylates, polyvinyl pyrrolidone, polyacrylamide, or combinations thereof.

7. The device of claim 1, wherein the radial rigidity of the device is slowly attenuated as its structural polymer is unlinked and metabolized such that the device slowly becomes more flexible causing adaptation and remodeling of the vessel and restoration of the vessel's elasticity.

8. A device for placement within a blood vessel to maintain or enhance blood flow through the blood vessel, the device comprising:

multiple, balloon-expandable, bioresorbable, vascular stent elements configured to be implanted in the blood vessel as a multi-element stent;

wherein at least two of the stent elements are configured to be positioned serially along a longitudinal length of a balloon with a space between the stent elements in an unexpanded state;

wherein at least two of the stent elements are configured to shorten upon balloon expansion to an expanded state at a target vessel location to create a space between the stent elements in the expanded state such that the stent elements do not touch one another at the target vessel location during skeletal movement;

wherein at least two of the stent elements are configured to be radially rigid after implantation at the target vessel location;

wherein a cell pattern of at least two of the stent elements is configured to shorten the stent elements upon expansion and provide the space between the stent elements in the expanded state; and wherein the stent elements comprise one or more shortening sections configured to shorten upon expansion to the expanded state and one or more lengthening sections configured to lengthen upon expansion to the expanded state.

9. The device of claim 8, wherein the stent elements are configured to be positioned serially along the longitudinal length of the balloon with the space between the stent elements in the unexpanded state of 1.77 mm or less.

10. The device of claim 8, wherein the one or more shortening sections comprise closed cells.

11. The device of claim 8, wherein the one or more shortening sections comprise open cells with one or more struts connecting one or more peaks of a first ring to one or more peaks of a second ring.

12. The device of claim 8, wherein the one or more lengthening sections comprise open cells with one or more struts connecting one or more valleys of a first ring to one or more valleys of a second ring.

13. The device of claim 8, wherein the cell pattern of at least two stent elements is tailored to maximize longitudinal and axial flexibility and forego radial force.

14. The device of claim 8, wherein at least two stent elements are formed from different bioresorbable polymer material.

15. The device of claim 8, wherein at least two elements vary in diameter.

* * * * *